US011431469B2

United States Patent
Masuda

(10) Patent No.: US 11,431,469 B2
(45) Date of Patent: Aug. 30, 2022

(54) TRANSMISSION DEVICE, RECEPTION DEVICE, AND TRANSCEIVER SYSTEM

(71) Applicant: Sony Semiconductor Solutions Corporation, Kanagawa (JP)

(72) Inventor: Takashi Masuda, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 0 days.

(21) Appl. No.: 17/271,835

(22) PCT Filed: Aug. 8, 2019

(86) PCT No.: PCT/JP2019/031312
§ 371 (c)(1),
(2) Date: Feb. 26, 2021

(87) PCT Pub. No.: WO2020/070974
PCT Pub. Date: Apr. 9, 2020

(65) Prior Publication Data
US 2021/0320783 A1    Oct. 14, 2021

(30) Foreign Application Priority Data

Oct. 2, 2018    (JP) .............................. JP2018-187721

(51) Int. Cl.
*H03D 3/24* (2006.01)
*H04L 7/06* (2006.01)
*H04L 7/00* (2006.01)

(52) U.S. Cl.
CPC .............. *H04L 7/06* (2013.01); *H04L 7/0012* (2013.01)

(58) Field of Classification Search
CPC ...... H04L 7/06; H04L 7/0012; H04N 21/2401
(Continued)

(56) References Cited

U.S. PATENT DOCUMENTS

| 2009/0257453 A1* | 10/2009 | Yanagisawa | ............ H03L 7/093 370/480 |
| 2010/0182402 A1 | 7/2010 | Nakajima et al. | |
| 2011/0043694 A1* | 2/2011 | Izuno | ................. H04N 21/2401 348/515 |

FOREIGN PATENT DOCUMENTS

| JP | 2001-230750 A | 8/2001 |
| JP | 2010-28261 A | 2/2010 |

(Continued)

OTHER PUBLICATIONS

International Search Report (PCT/ISA/210), International Application No. PCT/JP2019/031312, dated Sep. 24, 2019.

(Continued)

*Primary Examiner* — Phuong Phu
(74) *Attorney, Agent, or Firm* — Michael Best & Friedrich LLP

(57) ABSTRACT

An objective of the present technology is to provide a transmission device, a reception device, and a transceiver system of which miniaturization can be achieved. The transmission device includes an oscillator configured to oscillate a first clock signal; and a register signal reception unit configured to receive a register signal transmitted from a reception device and used for controlling the first clock signal. The reception device includes a signal generation unit configured to generate a register signal for controlling a first clock signal transmitted from the transmission device based on a comparison result obtained by comparing a reference clock signal with one of the first clock signal and a second clock signal which is based on the first clock signal; and a register signal transmission unit configured to transmit the register signal generated by the signal generation unit to the transmission device.

12 Claims, 14 Drawing Sheets

(58) Field of Classification Search
USPC ........ 375/373, 375, 376, 371, 325–327, 355
See application file for complete search history.

(56) References Cited

FOREIGN PATENT DOCUMENTS

| | | |
|---|---|---|
| JP | 2013-520081 A | 5/2013 |
| JP | 2017-175533 A | 9/2017 |
| WO | 2009-118884 A1 | 10/2009 |
| WO | 2018/061810 A1 | 4/2018 |

OTHER PUBLICATIONS

Notification of Transmittal of the International Search Report and the Written Opinion of the International Searching Authority, or the Declaration (PCT/ISA/220), International Application No. PCT/JP2019/031312, dated Oct. 8, 2019.

Written Opinion of the International Search Authority (PCT/ISA/237), International Application No. PCT/JP2019/031312, dated Oct. 8, 2019.

\* cited by examiner

TRANSMISSION DEVICE, RECEPTION DEVICE, AND TRANSCEIVER SYSTEM

TECHNICAL FIELD

The present technology relates to a transmission device, a reception device, and a transceiver system.

BACKGROUND ART

A transmitter has a reference clock signal and transmits a signal with a data rate of multiplication of the reference clock signal to a receiver. For example, an endoscope is configured such that the reference clock signal or a control signal is transmitted from a receiver to a transmitter.

CITATION LIST

Patent Literature

[PTL 1]
JP 2017-175533 A

SUMMARY

Technical Problem

However, when the number of signals transmitted and received between the transmitter and the receiver increases, the number of wirings between the transmitter and the receiver increases. Further, when the number of wirings between the transmitter and the receiver increases, the number of terminals of a semiconductor chip which has various functions of the transmitter increases. Therefore, there is a problem that it is difficult to achieve miniaturization of the transmitter.

An objective of the present technology is to provide a transmission device, a reception device, and a transceiver system of which miniaturization can be achieved.

Solution to Problem

To achieve the objective, a transmission device according to an aspect of the present technology includes: an oscillator configured to oscillate a first clock signal; and a control signal reception unit configured to receive a control signal transmitted from an external device and used for controlling the first clock signal.

To achieve the objective, a reception device according to another aspect of the present technology includes: a signal generation unit configured to generate a control signal for controlling a first clock signal transmitted from an external device based on a comparison result obtained by comparing a reference clock signal with one of the first clock signal and a second clock signal which is based on the first clock signal; and a signal transmission unit configured to transmit the control signal generated by the signal generation unit to the external device.

To achieve the objective, a transceiver system according to still another aspect of the present technology includes: a transmission device configured to transmit predetermined signals; and a reception device configured to receive the predetermined signals transmitted from the transmission device. The transmission device includes an oscillator that oscillates a first clock signal which is one of the predetermined signals, and a reception unit that receives a control signal transmitted from the reception device and used for controlling the first clock signal. The reception device includes a signal generation unit that generates the control signal based on a comparison result obtained by comparing a reference clock signal with one of the first clock signal transmitted from the transmission device and a second clock signal which is based on the first clock signal, and a signal transmission unit that transmits the control signal generated by the signal generation unit to the transmission device.

DESCRIPTION OF EMBODIMENTS

First Embodiment

A transmission device, a reception device, and a transceiver system according to a first embodiment of the present technology will be described with reference to FIGS. 1 to 3. First, a schematic configuration of the transmission device, the reception device, and the transceiver system according to the embodiment will be described with reference to FIG. 1. The transmission device, the reception device, and the transceiver system according to the embodiment are configured to transmit and receive data for transmission clock signals for synchronization in conformity with a source-synchronous scheme.

Figure 1:
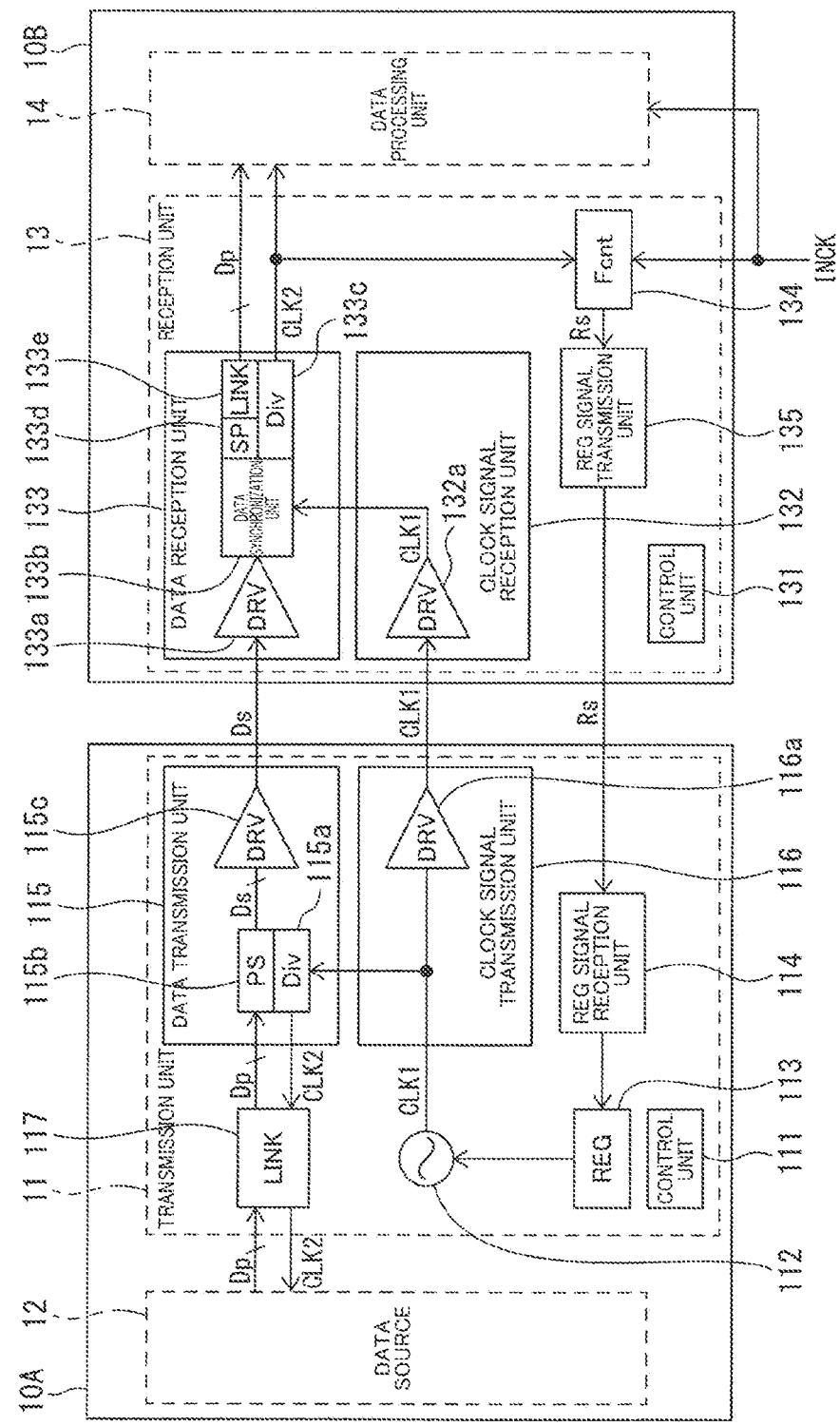
FIG. 1 is a functional block diagram illustrating a schematic configuration of a transmission device, a reception device, and a transceiver system according to a first embodiment of the present technology.

As illustrated in FIG. 1, a transceiver system 1 according to the embodiment includes a transmission device 10A that transmits a predetermined signal and a reception device 10B that receives the predetermined signal transmitted from the transmission device 10A. The transceiver system 1 can be applied to, for example, an endoscope system and is configured such that the transmission device 10A transmits captured data captured by the transmission device 10A to the reception device 10B. The reception device 10B processes the captured data transmitted from the transmission device 10A and transmits the processed captured data to, for example, a display device (not illustrated). Therefore, miniaturization of the transmission device 10A is achieved so that the transmission device 10A can enter a narrow region such as the inside of a human body. The reception device 10B has a configuration (which will be described below in detail) in which a clock signal can be controlled to receive the captured data from the miniaturized transmission device 10A and to cause the transmission device 10A to stably operate.

The transmission device 10A according to the embodiment includes a data source (which is an example of a data generation unit) 12 that generates data which is one of predetermined signals transmitted to the reception device 10B and a transmission unit 11 that transmits the data input from the data source 12 to an oscillator 112. In the embodiment, the transmission unit 11 and the data source 12 are formed in different semiconductor chips to be stacked. The transmission unit 11 and the data source 12 may be formed in the same semiconductor chip.

The data source 12 includes, for example, a solid-state image sensor (not illustrated). The data source 12 outputs captured data obtained by imaging an external environment in which the transmission device 10A is disposed, to the transmission unit 11.

As illustrated in FIG. 1, the transmission unit 11 included in the transmission device 10A includes the oscillator 112 that oscillates a first clock signal CLK1 and a register signal reception unit (which is an example of a control signal reception unit) 114 that receives a register signal (which is an example of a control signal) Rs transmitted from the reception device 10B and used for controlling the first clock signal CLK1. The reception device 10B corresponds to an example of an external device in the transmission device 10A. In FIG. 1 and the other figures, a register is notated as "REG".

The oscillator 112 is configured to change an oscillation frequency. Thus, the oscillator 112 can output the first clock signal CLK1 of which a frequency is changed. Unlike a phase locked loop (PLL), the oscillator 112 does not include a phase comparator, a loop filter, a voltage control oscillator, or a divider. Therefore, further miniaturization of the transmission device 10A can be achieved compared to a transmission device of the related art including a PLL.

The transmission unit 11 includes a register (which is an example of a storage unit) 113 that stores a setting value of the frequency of the first clock signal CLK1 oscillated by the oscillator 112. The register 113 stores a plurality of setting values associated for each frequency of the first clock signal CLK1. The register 113 reads the same setting values as the setting values included in the register signal Rs received by the register signal reception unit 114 and outputs the setting values to the oscillator 112. The oscillator 112 sets the setting values input from the register 113 in a predetermined region. Thus, the oscillator 112 oscillates the first clock signal CLK1 with the frequency corresponding to the setting value input from the register 113. The register 113 may store a setting value of each constituent element provided in the transmission device 10A as well as the setting values of the first clock signal CLK1.

When the register signal Rs transmitted from the reception device 10B is received, the register signal reception unit 114 acquires frequency height information included in the received register signal Rs. As will be described below in detail, the frequency height information is information indicating that the frequency of the first clock signal CLK1 is an optimum value or information indicating whether the frequency of the first clock signal CLK1 is higher or lower than the frequency of a reference clock signal INCK. A frequency difference between the first clock signal CLK1 and the reference clock signal INCK is detected in the reception device 10B. The register signal reception unit 114 outputs a setting value for lowering a current frequency of the first clock signal CLK1 to the register 113 when the frequency height information indicating that the frequency of the first clock signal CLK1 is higher than the frequency of the reference clock signal INCK is acquired. Conversely, the register signal reception unit 114 outputs a setting value for raising the current frequency of the first clock signal CLK1 to the register 113 when the frequency height information indicating that the frequency of the first clock signal CLK1 is lower than the frequency of the reference clock signal INCK is acquired.

The transmission unit 11 includes a clock signal transmission unit 116 that is connected to the oscillator 112 and transmits the first clock signal CLK1 to the reception device 10B. The clock signal transmission unit 116 includes a driver 116a that includes an input terminal connected to the oscillator 112. In FIG. 1 and other figures, the driver is notated as "DRV". The driver 116a outputs, for example, the first clock signal CLK1 of a single-ended mode input from the oscillator 112 with the single-ended mode remaining. Thus, the transmission unit 11 can achieve a reduction in the number of pins (the number of terminals) used for input and output or the like. The driver 116a can perform input and output impedance conversion when the driver 116a has, for example, a configuration of a voltage follower. Therefore, since output impedance is lowered, the driver 116a can achieve an improvement in an output current. Thus, the transmission device 10A can inhibit an erroneous operation caused due to a decrease in a signal level of the first clock signal CLK1 (that is, a signal waveform of the first clock signal CLK1 becoming blunt) output from the driver 116a in a wiring connecting the transmission device 10A to the reception device 10B.

The driver 116a may be configured to convert the first clock signal CLK1 input from the oscillator 112 from the single-ended mode to the differential mode and transmit the first clock signal CLK1 to the reception device 10B. In this case, the transmission unit 11 can transmit the first clock signal CLK1 with a higher frequency at a low voltage although the number of pins (the number of terminals) used for input and output or the like is greater by one than a case in which the first clock signal CLK1 of the single-ended mode is transmitted to the reception device 10B.

The transmission unit 11 includes a data transmission unit 115 that transmits data input from the data source 12 to the reception device 10B. The data transmission unit 115 includes a divider 115a that divides the first clock signal CLK1 input from the oscillator 112 to generate a second clock signal CLK2 with a lower frequency than the first clock signal CLK1. In FIG. 1 and other figures, the divider is notated as "Div". The divider 115a outputs the second clock signal CLK2 to the data source 12 via a link unit 117 (which will be described below in detail).

The data transmission unit 115 includes a parallel-serial conversion unit 115b that converts data Dp input in a parallel form from the data source 12 in synchronization with the second clock signal CLK2 into data Ds with a serial form synchronized with the first clock signal CLK1. In FIG. 1 and other figures, the parallel-serial conversion unit is notated as "PS". Further, the data transmission unit 115 includes a driver 115c (which is an example of a transmission driving unit) that transmits the data Ds with the serial form synchronized with the first clock signal CLK1 to the reception device 10B. The driver 115c outputs the data Ds of the single-ended mode input in synchronization with the first clock signal CLK1 from, for example, the parallel-serial conversion unit 115b with the single-ended mode remaining. Thus, the transmission unit 11 can achieve a reduction of the number of pins (the number of terminals) used for input and output or the like. The driver 115c can perform input and output impedance conversion when the driver 115c has, for example, a configuration of a voltage follower. Therefore, since output impedance is lowered, the driver 115c can achieve an improvement in an output current. Thus, the transmission device 10A can inhibit an erroneous operation caused due to a decrease in a signal level of the data Ds (that is, a signal waveform of the data Ds becoming blunt) output from the driver 115c in a wiring connecting the transmission device 10A to the reception device 10B.

The driver 115c may be configured to convert the data Ds input from the parallel-serial conversion unit 115b from the single-ended mode to the differential mode and transmit the data Ds to the reception device 10B. In this case, the transmission unit 11 can transmit the data Ds at a low voltage although the number of pins (the number of terminals) used for input and output or the like is greater by one than in a case in which the data Ds of the single-ended mode is transmitted to the reception device 10B in synchronization with the first clock signal CLK1 with the high frequency.

The transmission unit 11 includes a link unit 117 provided between the data source 12 and the data transmission unit 115. The link unit 117 outputs the second clock signal CLK2 input from the data transmission unit 115 to the data source 12. The link unit 117 performs a predetermined process on the data input from the data source 12 in synchronization with the second clock signal CLK2 and outputs the data Dp with a parallel form to the data transmission unit 115 in synchronization with the second clock signal CLK2.

The transmission unit 11 includes a control unit 111. The control unit 111 generally controls the oscillator 112, the register 113, the register signal reception unit 114, the data transmission unit 115, the clock signal transmission unit 116, and the link unit 117. The control unit 111 may also be configured to control the data source 12.

The reception device 10B according to the embodiment includes a reception unit 13 that receives the predetermined signal transmitted from the transmission device 10A and a data processing unit 14 that performs a predetermined process on the data received by the reception unit 13. In the embodiment, the reception unit 13 and the data processing unit 14 are formed in different semiconductor chips to be stacked. The reception unit 13 and the data processing unit 14 may be formed in the same semiconductor chip.

The reception unit 13 included in the reception device 10B includes a clock signal reception unit 132 that receives the first clock signal CLK1 transmitted from the transmission device 10A. The transmission device 10A corresponds to an example of an external device of the reception device 10B. The clock signal reception unit 132 includes a driver 132a connected to the clock signal transmission unit 116 provided in the transmission unit 11 of the transmission device 10A. The driver 132a is connected to the driver 116a provided in the clock signal transmission unit 116. The driver 132a has a role of amplifying the input first clock signal CLK1 and outputs the amplified first clock signal CLK1 to a data synchronization unit 133b (which will be described below in detail) at the rear stage.

When the driver 116a of the clock signal transmission unit 116 is configured to output the first clock signal CLK1 of the differential mode, the driver 132a has a role of converting the first clock signal CLK1 transmitted in the differential mode into the single-ended mode and outputting the converted first clock signal CLK1 to the data synchronization unit 133b at the rear stage.

The reception unit 13 includes a data reception unit 133 that receives the data Ds transmitted from the transmission device 11A in synchronization with the first clock signal CLK1. The data reception unit 133 is connected to an output terminal of the driver 132a of the clock signal reception unit 132. Thus, the first clock signal CLK1 output from the clock signal reception unit 132 is input to the data reception unit 133.

The data reception unit 133 includes a driver 133a to which the data Ds transmitted from the driver 115c provided in the data transmission unit 115 of the transmission device 11A is input. The driver 133a has a role of amplifying the input data Ds and outputting the amplified data Ds to the data synchronization unit 133b at the rear stage.

When the driver 115c of the data transmission unit 115 is configured to output the data Ds of the differential mode, the driver 133a has a role of converting the data Ds of the differential mode input from the driver 115c into the data Ds of the single-ended mode and outputting the converted data Ds to the data synchronization unit 133b at the rear stage.

The data reception unit 133 includes the data synchronization unit (which is an example of a storage unit) 133b that temporarily stores the data Ds transmitted from the transmission device 10A in synchronization with the first clock signal CLK1. The data synchronization unit 133b is configured as a flip-flop circuit. An input terminal of the data synchronization unit 133b is connected to an output terminal of the driver 133a. The data synchronization unit 133b temporarily retains the data Ds input from the driver 133a in synchronization with the first clock signal CLK1. There is a possibility of the phase of the data Ds transmitted from the transmission device 10A deviating from the phase of the first clock signal CLK1. Therefore, the data synchronization unit 133b adjusts the phases of the data Ds and the first clock signal CLK1 by temporarily retaining (that is, latching) the data Ds in synchronization with the first clock signal CLK1. In this way, the data synchronization unit 133b functions as a phase adjustment unit.

The data reception unit 133 has a divider 133c that divides the frequency of the first clock signal CLK1 input from the transmission device 10A and generates the second clock signal CLK2 with a lower frequency than the first clock signal CLK. The divider 133c has the same configuration as the divider 115a provided in the data transmission unit 115 of the transmission device 10A. The divider 133c divides the first clock signal CLK1 to generate the second clock signal CLK2 with the same frequency as the second clock signal CLK2 generated by the divider 115a.

The data reception unit 133 includes a serial-parallel conversion unit 133d that converts the data Ds input in a serial form from the transmission device 10A in synchronization with the first clock signal CLK1 into the data Dp with a parallel form synchronized with the second clock signal CLK2. In FIG. 1 and the other figures, the serial-parallel conversion unit is notated as "SP". The serial-parallel conversion unit 133d converts the data Ds with the serial form temporarily stored in the data synchronization unit 133b into the data Dp with the parallel form in synchronization with the second clock signal CLK2 generated by the divider 133c.

The data reception unit 133 includes a link unit 133e to which the data Dp output in the parallel form from the serial-parallel conversion unit 133d is input in synchronization with the second clock signal CLK2. The link unit 133e converts the data Dp input from the serial-parallel conversion unit 133d into a data form which can be processed by the data processing unit 14 (which will be described below in detail).

The data reception unit 133 outputs the second clock signal CLK2 from the divider 133c to the data processing unit 14 and outputs the data Dp with the parallel form from the link unit 133e to the data processing unit 14. Thus, the data reception unit 133 can output the second clock signal CLK2 generated by the divider 133c and the data Dp output from the serial-parallel conversion unit 133d and synchronized with the second clock signal CLK2 to the data processing unit 14.

In this way, the data Dp output from the data reception unit 133 is a signal synchronized with the second clock signal CLK2 generated by the divider 133c. The data Dp input to the data transmission unit 115 is a signal synchronized with the second clock signal CLK2 generated by the divider 115a. However, the second clock signal CLK2 generated by the divider 115a of the data transmission unit 115 and the second clock signal CLK2 generated by the divider 133c of the data reception unit 133 differ in phase and do not have the same timing, strictly speaking. In the embodiment, the second clock signal CLK2 generated by the divider 115a and the second clock signal CLK2 generated by the divider 133c are signals with the same frequency and can also be signals with different frequencies. For example, the data transmission unit 115 of the transmission unit 11 is configured to convert the data Dp input at a communication speed of 50 Mbps/20 bits (the frequency of the second clock signal CLK2 generated by the divider 115a is 50 MHz) into the data Ds of which a communication speed is 1 Gbps/1 bit. In this case, the data reception unit 133 of the reception unit 13 may be configured to convert the data Ds input at a communication speed of 1 Gbps/1 bit (the frequency of the second clock signal CLK2 generated by the divider 133c is 10 MHz) into the data Dp of which a communication speed is 100 Mbps/10 bits.

The reception unit 13 includes a signal generation unit 134 that generates a register signal (which is an example of a control signal) Rs for controlling the first clock signal CLK1 based on a comparison result obtained by comparing the reference clock signal INCK with one of the first clock signal CLK1 transmitted from the transmission device 10A and the second clock signal CLK2 which is based on the first clock signal CLK1. Here, the second clock signal CLK2 is a signal generated by dividing the first clock signal CLK1, and therefore corresponds to a signal which is based on the first clock signal CLK1. In FIG. 1 and the other figures, the signal generation unit is notated as "Fcnt". The reception unit 13 includes a register signal transmission unit (which is an example of a signal transmission unit) 135 that transmits the register signal Rs generated by the signal generation unit 134 to the transmission device 10A.

The second clock signal CLK2 output from the divider 133c and the reference clock signal INCK input from the outside of the reception device 10B are input to the signal generation unit 134. The signal generation unit 134 continues to compare the input second clock signal CLK2 with the frequency of the reference clock signal INCK sequentially. The signal generation unit 134 includes, for example, a counter that operates with the second clock signal CLK2 and a counter that operates with the reference clock signal INCK. The signal generation unit 134 compares a count value counted by each counter within a predetermined period and acquires a frequency difference between the second clock signal CLK2 and the reference clock signal INCK. The signal generation unit 134 outputs the register signal Rs to the register signal transmission unit 135 when the frequency difference between the second clock signal CLK2 and the reference clock signal INCK is out of a predetermined error range. The register signal Rs includes frequency height information.

The register signal transmission unit 135 includes an input terminal connected to the output terminal of the signal generation unit 134 and an output terminal connected to the input terminal of the register signal reception unit 114 included in the transmission device 10A via a wiring. When the register signal Rs is input from the signal generation unit 134, the register signal transmission unit 135 outputs the register signal Rs to the register signal reception unit 114 via the wiring.

The reception unit 13 includes a control unit 131. The control unit 131 generally controls the clock signal reception unit 132, the data reception unit 133, the signal generation unit 134, and the register signal transmission unit 135.

The data processing unit 14 included in the reception device 10B performs a predetermined process using the data Dp input from the data reception unit 133, the second clock signal CLK2, and the reference clock signal INCK input from the outside of the reception device 10B. For example, the data processing unit 14 performs a sorting process, a correction process, or the like on the data Dp to display an image captured in the data source 12 on a display device (not illustrated).

Next, an example of a data format of a data signal of the register signal Rs transmitted and received between the transmission device 10A and the reception device 10B will be described with reference to FIG. 2. For example, Manchester coding may be used as the data format.

Figure 2:
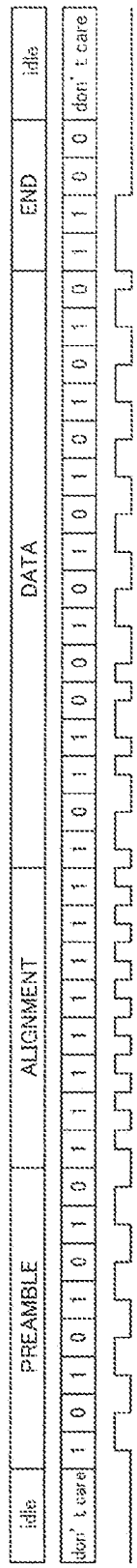
FIG. 2 is a diagram illustrating an example of a format of data transmitted and received in the transmission device, the reception device, and the transceiver system according to the first embodiment of the present technology.

As illustrated in FIG. 2, the data format includes four portions: a preamble, an alignment, data, and an end. A clock signal is embedded in the preamble portion. Therefore, a period of the transmitted register signal Rs can be obtained by performing over-sampling on the preamble portion with a clock signal with a high frequency. Thus, the transmission device 10A can recognize a period at which the register signal Rs is transmitted. In the alignment portion, bits are synchronized at the period obtained from the preamble portion. In the embodiment, for example, all the signals of "1" are set in the alignment portion. Thus, the transmission device 10A can take a transmission period and synchronization using the clock signal which is transmitted by the oscillator 112 and has a higher frequency than the register signal Rs.

In the data portion, the register signal Rs transmitted from the reception device 10B to the transmission device 10A is set. In the data portion, the register signal Rs is set in conformity with a predetermined rule. Thus, the transmission device 10A can acquire information of the register signal Rs set in the data portion and recognize content of information. In the end portion, information indicating that the transmission of the register signal Rs at the period ends is set. Thus, the transmission device 10A can recognize that the transmission of the data signal at the period ends.

In the source-synchronous scheme, the data signal and the clock signal are transmitted side by side between the transmission device 10A and the reception device 10B. Therefore, the preamble portion may not be provided in the data format for transmitting the register signal Rs. In this case, phase adjustment is performed on the alignment of the bits on the side of the reception device 10B.

Next, a control process for the frequency of the clock signal in the transmission device 10A, the reception device 10B, and the transceiver system 1 according to the embodiment will be described with reference to FIGS. 3 and 4 in addition to FIG. 1. FIG. 3 is a sequence diagram illustrating a control process for the frequency of the clock signal performed during activation of the transceiver system 1. FIG. 4 is a sequence diagram illustrating a control process for the frequency of the clock signal performed during an operation after the activation of the transceiver system 1. In the embodiment, to facilitate understanding, a processing flow of the transceiver system 1 is divided into operations during activation and after the activation. However, in the processing flow of the transceiver system 1, a process during an operation after the activation and continuously after the end of the process during the activation may be, of course, performed.

In the transceiver system 1 according to the embodiment, the process performed during activation is initially started by feeding power to the transmission device 10A and the reception device 10B.

(Step S1)

Figure 3:
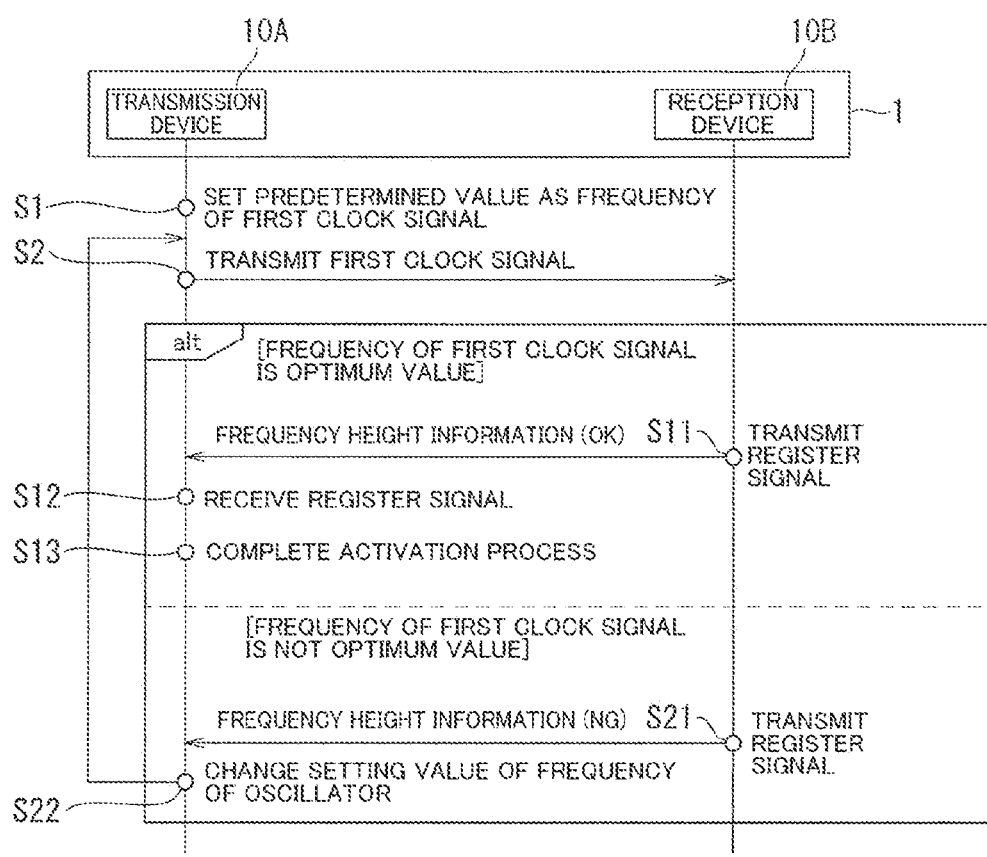
FIG. 3 is a sequence diagram (part 1) illustrating control of a frequency of a clock signal oscillated by the transmission device in the transceiver system according to the first embodiment of the present technology.
Figure 4:
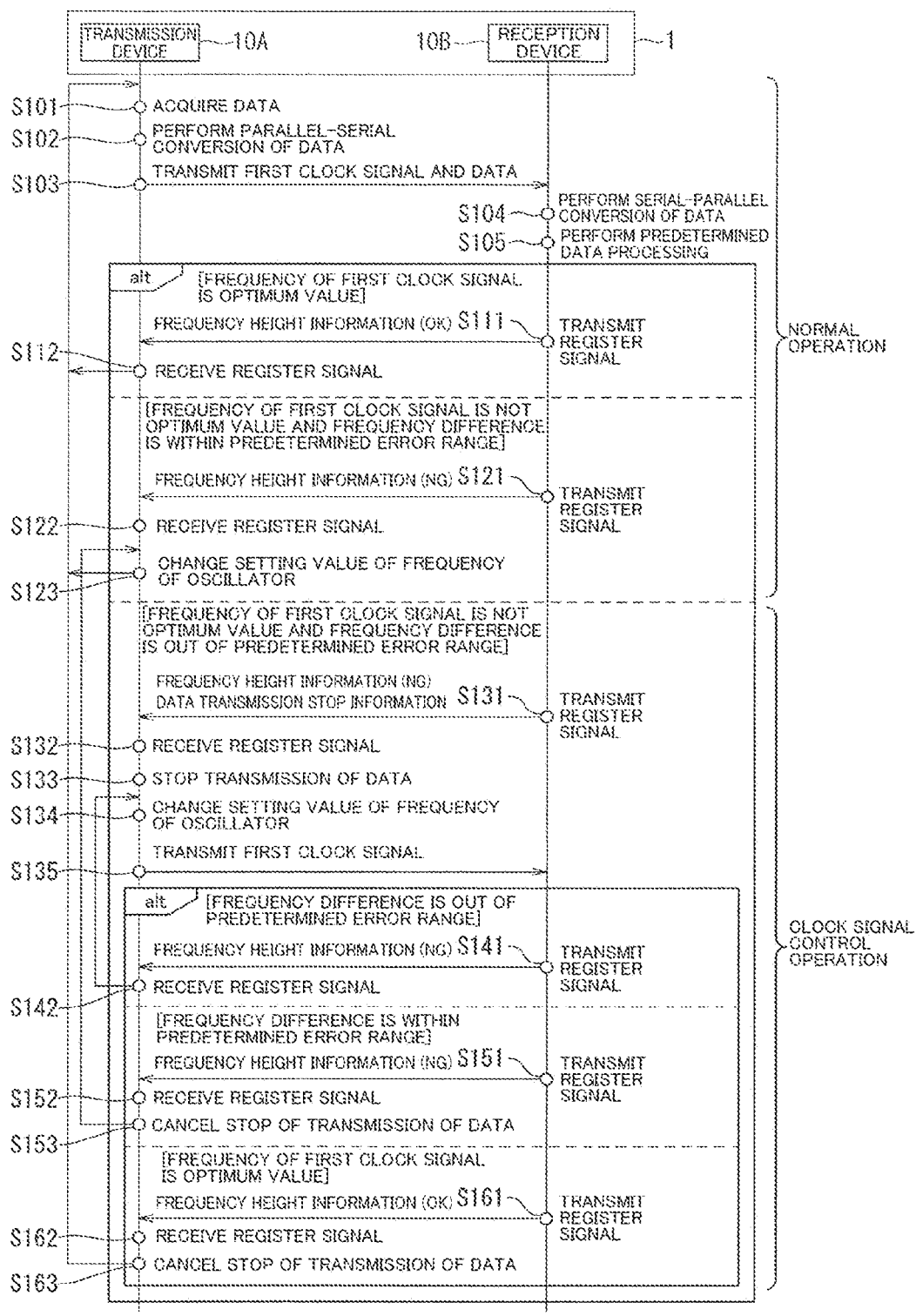
FIG. 4 is a sequence diagram (part 2) illustrating control of a frequency of a clock signal oscillated by the transmission device in the transceiver system according to the first embodiment of the present technology.

As illustrated in FIG. 3, in step S1, the transmission device 10A sets a predetermined value as the frequency of the first clock signal CLK1 and the process proceeds to step S2. The control unit 111 of the transmission device 10A sets an initial value (for example, a designed value) of the frequency of the first clock signal CLK1 as a predetermined value in the setting value of the oscillator 112.

(Step S2)

In step S2, the transmission device 10A outputs the first clock signal CLK1 with the frequency of the predetermined value set in step S1 to the reception device 10B. The clock signal transmission unit 116 transmits the first clock signal CLK1 input from the oscillator 112 under the control of the control unit 111 to the reception device 10B.

The transceiver system 1 performs a control process on the first clock signal CLK1 transmitted from the transmission device 10A to the reception device 10B continuously from step S2. In the control process for the first clock signal CLK1, the reception device 10B first performs a clock signal comparison process of comparing the reference clock signal INCK with the second clock signal CLK2 generated from the first clock signal CLK1 transmitted from the transmission device 10A. In accordance with a result of the clock signal comparison process, the reception device 10B performs one of the processes of steps S11 and S21. In the clock signal comparison process, the signal generation unit 134 acquires a difference between the frequency of the reference clock signal INCK input from the outside of the reception device 10B and the frequency of the second clock signal CLK2 input from the data reception unit 133 under the control of the control unit 131.

(Step S11)

As a result of the clock signal comparison process in the signal generation unit 134, it is assumed that the frequencies of the second clock signal CLK2 and the reference clock signal INCK match. Alternatively, as a result of the clock signal comparison process in the signal generation unit 134, it is assumed that the frequency difference between the second clock signal CLK2 and the reference clock signal INCK is less than a resolution of the frequency which can be set in the oscillator 112. In this case, the control unit 131 determines that the frequency of the first clock signal CLK1 transmitted from the transmission device 10A is an optimum value. Thus, in step S11, the reception device 10B transmits the register signal Rs to the transmission device 10A. The signal generation unit 134 includes frequency height information indicating that the frequency of the first clock signal CLK1 is the optimum value, in the register signal Rs. In FIGS. 3 and 4, the frequency height information indicating that the frequency of the first clock signal CLK1 is the optimum value is notated as "frequency height information (OK)".

(Step S12)

The transceiver system 1 performs a process of step S12 continuously from step S11. As illustrated in FIG. 3, the transmission device 10A receives the register signal Rs transmitted from the reception device 10B and analyzes the information included in the received register signal Rs, and then the process proceeds to step S13.

(Step S13)

In step S13, when the register signal Rs transmitted from the reception device 10B includes the frequency height information indicating that the frequency of the first clock signal CLK1 is the optimum value, the control unit 111 transitions to a state in which the process of activating the transmission device 10A is completed. Thus, the process during activation of the transmission device 10A and the reception device 10B ends and the transmission device 10A starts an operation process after the activation (which will be described below in detail).

(Step S21)

As a result of the clock signal comparison process in the control process for the first clock signal CLK1, it is assumed that the frequency difference between the reference clock signal INCK and the second clock signal CLK2 is greater than the resolution of the frequency which can be set in the oscillator 112. In this case, the control unit 131 determines that the frequency of the first clock signal CLK1 transmitted from the transmission device 10A is not the optimum value. Thus, in step S21, the reception device 10B transmits the register signal Rs to the transmission device 10A. The signal generation unit 134 includes frequency height information indicating that the frequency of the first clock signal CLK1 is not the optimum value, in the register signal Rs. In FIG. 3, the frequency height information indicating that the frequency of the first clock signal CLK1 is not the optimum value is notated as "frequency height information (NG)".

(Step S22)

The transceiver system 1 performs a process of step S22 continuously from step S21. As illustrated in FIG. 3, in step S22, the transmission device 10A changes the setting value of the oscillator 112 and the process proceeds to step S2. The control unit 111 reads a setting value newly set in the oscillator 112 from the register 113 based on the frequency height information included in the register signal Rs received by the register signal reception unit 114 and the setting value currently set in the oscillator 112. The control unit 111 sets the read setting value in the oscillator 112. Then, the changing of the setting value in the oscillator 112 is completed.

In step S2 after step S22, the first clock signal CLK1 with the frequency corresponding to the setting value newly set in step S22 is transmitted from the transmission device 10A to the reception device 10B. Thereafter, in the process during activation of the transceiver system 1 (that is, during activation of the transmission device 10A and the reception device 10B), the processes from step S11 to S13 or steps S21 and S22 are performed and the process during activation ends at a time point at which the frequency of the first clock signal CLK1 becomes the optimum value.

Next, a process performed during operation after the activation of the transceiver system 1 (that is, during operation after the activation of the transmission device 10A and the reception device 10B), which is performed after the end of the process during activation of the transceiver system 1 (that is, during activation of the transmission device 10A and the reception device 10B), will be described with reference to FIG. 4.

(Step S101)

As illustrated in FIG. 4, in step S101, the transmission device 10A starts acquiring data in the data source 12, and the process proceeds to step S102. In step S101, the data source 12 outputs the acquired data Dp to the link unit 117 in synchronization with the second clock signal CLK2. The link unit 117 outputs the data Dp input from the data source 12 to the data transmission unit 115 under the control of the control unit 111.

(Step S102)

In step S102, the transmission device 10A changes the data Dp in the parallel form into the data Ds in the serial form, and the process proceeds to step S103. The parallel-serial conversion unit 115b of the data transmission unit 115 outputs the data Ds synchronized with the first clock signal CLK1 input from the oscillator 112 to the driver 115c under the control of the control unit 111.

(Step S103)

In step S103 the transmission device 10A outputs the first clock signal CLK1 and the data Ds to the reception device 10B. The clock signal transmission unit 116 transmits the first clock signal CLK1 input from the oscillator 112 to the reception device 10B under the control of the control unit 111. After the process during activation of the transceiver system 1 (that is, during activation of the transmission device 10A and the reception device 10B) ends, the first clock signal CLK1 is continuously transmitted to the reception device 10B before the data Ds is transmitted in step S103. The frequency of the first clock signal CLK1 transmitted in step S103 is a frequency corresponding to the setting value set finally in the process during activation of the transceiver system 1 (that is, during activation of the transmission device 10A and the reception device 10B). The data transmission unit 115 transmits the data Ds to the reception device 10B under the control of the control unit 111.

(Step S104)

The transceiver system 1 performs a process of step S104 continuously from step S103. As illustrated in FIG. 3, in step S104, the reception device 10B converts the data Ds with the serial form transmitted from the transmission device 10A into the data Dp with the parallel form, and the process proceeds to step S105. The data reception unit 133 of the reception device 10B converts the data Dp transmitted from the transmission device 10A into the data Dp synchronized with the second clock signal CLK2 under the control of the control unit 131. In the data reception unit 133, the link unit 133e converts the data Dp input from the serial-parallel conversion unit 133d into a data form which can be processed by the data processing unit 14 under the control of the control unit 131. Further, the data reception unit 133 outputs the data Dp synchronized with the second clock signal CLK2 to the data processing unit 14 and outputs the second clock signal CLK2 to the data processing unit 14 and the signal generation unit 134 under the control of the control unit 131.

(Step S105)

In step S105, the reception device 10B performs predetermined data processing and the process proceeds to a control process for the first clock signal CLK1 after step S111. The data processing unit 14 performs a predetermined process using the data Dp input from the data reception unit 133.

In the control process for the first clock signal CLK1, the reception device 10B first performs a clock signal comparison process of comparing the reference clock signal INCK with the second clock signal CLK2 generated from the first clock signal CLK1 transmitted from the transmission device 10A. The reception device 10B performs one process of steps S111, S121, and S131 in accordance with a result of the clock signal comparison process.

(Step S111)

In the clock signal comparison process, the signal generation unit 134 acquires a difference between the frequency of the second clock signal CLK2 input from the data reception unit 133 and the frequency of the reference clock signal INCK input from the outside of the reception device 10B under the control of the control unit 131. As a result of the clock signal comparison process in the signal generation unit 134, it is assumed that the frequencies of the second clock signal CLK2 and the reference clock signal INCK match. Alternatively, as a result of the clock signal comparison process in the signal generation unit 134, it is assumed that the frequency difference between the second clock signal CLK2 and the reference clock signal INCK is less than a resolution of the frequency which can be set in the oscillator 112. In this case, the control unit 131 determines that the frequency of the first clock signal CLK1 transmitted from the transmission device 10A is an optimum value. Thus, in step S11, the reception device 10B transmits the register signal Rs to the transmission device 10A. The signal generation unit 134 includes frequency height information indicating that the frequency of the first clock signal CLK1 is the optimum value, in the register signal Rs.

(Step S112)

The transceiver system 1 performs a process of step S112 continuously from step S111. As illustrated in FIG. 4, the transmission device 10A receives the register signal Rs transmitted from the reception device 10B and analyzes the information included in the received register signal Rs. The control unit 111 determines that the information indicating that the frequency of the first clock signal CLK1 is the optimum value is included in the register signal Rs, and the process proceeds to step S101. In this way, until it is determined that the frequency of the first clock signal CLK1 is not the optimum value, steps S101 to S122 are repeatedly performed.

(Step S121)

When the frequency of the first clock signal CLK1 is not the optimum value and the frequency difference between the second clock signal CLK2 and the reference clock signal INCK is within a predetermined error range as the result of the clock signal comparison process in the control process of the first clock signal CLK1, step S121 is performed. Thus, in step S121, the reception device 10B transmits the register signal Rs to the transmission device 10A. The signal generation unit 134 includes frequency height information indicating that the frequency of the first clock signal CLK1 is not the optimum value and the frequency difference is within the predetermined error range, in the register signal Rs. In FIG. 4, the frequency height information indicating that the frequency of the first clock signal CLK1 is not the optimum value and the frequency difference is within the predetermined error range is noted as "frequency height information (NG)".

When the frequency of the second clock signal CLK2 is determined to be higher than the frequency of the reference clock signal INCK, the signal generation unit 134 includes information for giving an instruction to select a setting value with which the frequency of the first clock signal CLK1 oscillated by the oscillator 112 is lowered, in the frequency height information. Conversely, when the frequency of the second clock signal CLK2 is determined to be lower than the frequency of the reference clock signal INCK, the signal generation unit 134 includes information for giving an instruction to select a setting value with which the frequency of the first clock signal CLK1 oscillated by the oscillator 112 is raised, in the frequency height information. The signal generation unit 134 may include information for giving an instruction to raise (or lower) the frequency of the first clock signal CLK1 oscillated by the oscillator 112, in the frequency height information or may include the setting value associated with an oscillation frequency of the oscillator 112 in the frequency height information.

(Step S122)

The transceiver system 1 performs a process of step S122 continuously from step S121. As illustrated in FIG. 4, the transmission device 10A receives the register signal Rs transmitted from the reception device 10B and analyzes the information included in the received register signal Rs, and the process proceeds to step S123.

(Step S123)

The register signal Rs transmitted from the reception device 10B includes frequency height information indicating that the frequency of the first clock signal CLK1 is not the optimum value and the frequency difference is within a predetermined error range. Therefore, in step S123, the control unit 111 reads the setting value newly set in the oscillator 112 from the register 113 based on the frequency height information included in the register signal Rs received by the register signal reception unit 114 and the setting value currently set in the oscillator 112. The control unit 111 sets the read setting value in the oscillator 112, and the process proceeds to step S101. Thus, the changing of the setting value in the oscillator 112 is completed.

After step S101 after step S123, the first clock signal CLK1 with the frequency corresponding to the setting value newly set in step S123 is transmitted from the transmission device 10A to the reception device 10B (step S103).

(Step S131) When the frequency of the first clock signal CLK1 is not the optimum value and the frequency difference between the second clock signal CLK2 and the reference clock signal INCK is out of the predetermined error range as the result of the clock signal comparison process in the control process of the first clock signal CLK1, step S131 is performed. Thus, in step S131, the reception device 10B transmits the register signal Rs to the transmission device 10A. The signal generation unit 134 includes frequency height information indicating that the frequency of the first clock signal CLK1 is not the optimum value and the frequency difference is out of the predetermined error range, in the register signal Rs. In FIG. 4, the frequency height information indicating that the frequency of the first clock signal CLK1 is not the optimum value and the frequency difference is out of the predetermined error range is noted as "frequency height information (NG)".

When the frequency of the second clock signal CLK2 is determined to be higher than the frequency of the reference clock signal INCK, the signal generation unit 134 includes information for giving an instruction to select a setting value with which the frequency of the first clock signal CLK1 oscillated by the oscillator 112 is lowered, in the frequency height information. Conversely, when the frequency of the second clock signal CLK2 is determined to be lower than the frequency of the reference clock signal INCK, the signal generation unit 134 includes information for giving an instruction to select a setting value with which the frequency of the first clock signal CLK1 oscillated by the oscillator 112 is raised, in the frequency height information. The signal generation unit 134 may include information for giving an instruction to raise (or lower) the frequency of the first clock signal CLK1 oscillated by the oscillator 112, in the frequency height information or may include the setting value associated with an oscillation frequency of the oscillator 112 in the frequency height information.

Further, the signal generation unit 134 includes data transmission stop information in the register signal Rs. The data transmission stop information is information for stopping the transmission of the data Ds from the transmission device 10A to the reception device 10B. Thus, until the frequency difference between the second clock signal CLK2 and the reference clock signal INCK is within the predetermined error range, the transmission of the data Ds from the transmission device 10A to the reception device 10B is stopped.

(Step S132)

The transceiver system 1 performs a process of step S132 continuously from step S131. As illustrated in FIG. 4, the transmission device 10A receives the register signal Rs transmitted from the reception device 10B and analyzes the information included in the received register signal Rs, and then the process proceeds to step S133.

(Step S133)

When it is determined in step S132 that the register signal Rs transmitted from the reception device 10B includes the data transmission stop information, the transmission device 10A stops the transmission of the data Dp to the reception device 10B in step S133, and the process proceeds to step S134. The control unit 111 of the transmission device 10A stops, for example, the operation of the link unit 117 and stops the transmission of the data Ds to the reception device 10B so that the data Dp is not input to the data transmission unit 115.

(Step S134)

In step S134, the transmission device 10A changes the setting value of the oscillator 112, and the process proceeds to step S135. The control unit 111 reads a setting value newly set in the oscillator 112 from the register 113 based on the frequency height information included in the register signal Rs received by the register signal reception unit 114 and the setting value currently set in the oscillator 112. The control unit 111 sets the read setting value in the oscillator 112. Then, the setting value in the oscillator 112 is changed.

(Step S135)

In step S135, the transmission device 10A starts transmitting the first clock signal CLK1 of which the frequency is changed from the clock signal transmission unit 116 to the reception device 10B.

In the transceiver system 1, continuously from step S135, the reception device 10B performs a clock signal comparison process of comparing the frequency of the reference clock signal INCK with the frequency of the first clock signal CLK1 transmitted from the transmission device 10A. The reception device 10B performs one process of steps S141, S151, and S161 in accordance with a result of the clock signal comparison process.

(Step S141)

When it is determined that the frequency difference between the second clock signal CLK2 and the reference clock signal INCK is out of the predetermined error range as the result of the clock signal comparison process, step S141 is performed. Thus, since the process of step S141 is the same as the process of step S131 except that the register signal Rs does not include the data transmission stop information, description thereof will be omitted. When it is determined in the clock signal comparison process of step S141 that the frequency difference between the second clock signal CLK2 and the reference clock signal INCK is out of the predetermined error range, the reception device 10B transmits the register signal Rs to the transmission device 10A. Since the process of step S141 is the same as the process of step S131, description thereof will be omitted. The process in the flow of steps S141 and S142 is performed when the control for changing the frequency of the first clock signal CLK1 does not end (the changing is not completed).

(Step S142)

The transceiver system 1 performs a process of step S142 continuously from step S141. As illustrated in FIG. 4, the transmission device 10A receives the register signal Rs transmitted from the reception device 10B and analyzes the received register signal Rs. When the control unit 111 determines that the register signal Rs including the frequency height information indicating that the frequency difference between the second clock signal CLK2 and the reference clock signal INCK is out of the predetermined error range is received, the process proceeds to step S134. Thus, the control unit 111 newly sets the frequency of the first clock signal CLK1 based on the frequency height information included in the received register signal Rs (step S134), stops the transmission of the data Ds to the reception device 10B, and performs the process subsequent to step S135.

(Step S151)

In the transceiver system 1, continuously from step S135, the reception device 10B performs the clock signal comparison process of comparing the frequency of the reference clock signal INCK with the frequency of the first clock signal CLK1 transmitted from the transmission device 10A. When it is determined that the frequency difference between the second clock signal CLK2 and the reference clock signal INCK is within the predetermined error range as a result of the clock signal comparison process, the process of step S151 is performed. Since the process of step S151 is the same as the process of step S121 except that the register signal Rs includes cancellation information of the data transmission stop, description thereof will be omitted.

(Step S152)

The transceiver system 1 performs a process of step S152 continuously from step S151. As illustrated in FIG. 4, the transmission device 10A receives the register signal Rs transmitted from the reception device 10B and analyzes the received register signal Rs. When the control unit 111 determines that the register signal Rs including the frequency height information indicating that the frequency difference between the second clock signal CLK2 and the reference clock signal INCK is within the predetermined error range and the cancellation information of the data transmission stop is received, the process proceeds to step S153.

(Step S153)

When it is determined in step S152 that the register signal Rs transmitted from the reception device 10B includes the data transmission stop information, the transmission device 10A cancels the stop of the transmission of the data Dp to the reception device 10B in step S153, and the process proceeds to step S123. The control unit 111 of the transmission device 10A resumes, for example, the operation of the link unit 117 and cancels the stop of the transmission of the data Ds to the reception device 10B so that the data Dp is input to the data transmission unit 115.

The control unit 111 newly sets the frequency of the first clock signal CLK1 based on the frequency height information included in the received register signal Rs (step S123), resumes the transmission of the data Ds to the reception device 10B, and performs the process subsequent to step S101. The process of the flow from steps S151 to S153 is performed when the control for changing the frequency of the first clock signal CLK1 ends (the changing is completed) but when the adjustment of the frequency of the first clock signal CLK1 does not end (the adjustment is not completed).

(Step S161)

In the transceiver system 1, continuously from step S135, the reception device 10B performs the clock signal comparison process of comparing the frequency of the reference clock signal INCK with the frequency of the first clock signal CLK1 transmitted from the transmission device 10A. When it is determined that the frequency of the first clock signal CLK1 matches the optimum value as the result of the clock signal comparison process, the process of step S161 is performed. Since the process of step S161 is similar to the process of step S111 except that the register signal Rs includes the cancellation information of the data transmission stop, description thereof will be omitted.

(Step S162)

The transceiver system 1 performs a process of step S162 continuously from step S161. As illustrated in FIG. 4, the transmission device 10A receives the register signal Rs transmitted from the reception device 10B and analyzes the received register signal Rs. When the control unit 111 determines that the register signal Rs including the frequency height information indicating that the frequency of the first clock signal CLK1 matches the optimum value and the cancellation information of the data transmission stop is received, the process proceeds to step S163.

(Step S163)

When it is determined in step S162 that the register signal Rs transmitted from the reception device 10B includes the data transmission stop information, the transmission device 10A cancels the stop of the transmission of the data Dp to the reception device 10B in step S163, and the process proceeds to step S101. The control unit 111 of the transmission device 10A resumes, for example, the operation of the link unit 117 and cancels the stop of the transmission of the data Ds to the reception device 10B so that the data Dp is input to the data transmission unit 115.

The control unit 111 resumes the transmission of the data Ds to the reception device 10B with a current value maintaining as the frequency of the first clock signal CLK1 based on the frequency height information included in the received register signal Rs and performs the process subsequent to step S101. The process of the flow from steps S161 to S163 is performed when the control for adjusting the frequency of the first clock signal CLK1 ends (the adjustment is completed).

The flow of steps S101 to S105 and steps S111 to S112 or steps S121 and S123 after the end of the process during activation of the transceiver system 1 (that is, during activation of the transmission device 10A and the reception device 10B) is a flow of a normal operation of the transceiver system 1, the transmission device 10A, and the reception device 10B. Here, the normal operation is an operation of transmitting and receiving the signal between the transmission device 10A and the reception device 10B in a state in which the first clock signal CLK1 is synchronized with the data Ds. The flow of steps S101 to S105 and steps S111 to S112 or steps S121 to S123 after step S163 is a flow of a normal operation of the transceiver system 1, the transmission device 10A, and the reception device 10B.

The operation of the flow from steps S131 to S135, steps S141 to S142, steps S151 to S153, or steps S161 to S163 corresponds to a clock signal control operation of controlling the frequency of the first clock signal CLK1. The transceiver system 1 is driven until the frequency difference between the second clock signal CLK2 and the reference clock signal INCK becomes within the predetermined error range from out of the predetermined error range and the frequency of the first clock signal CLK1 becomes the optimum value. The transceiver system 1 performs the process from steps S101 to S105 after proceeding from step S163 to step S101, and the normal operation or the clock signal control operation in accordance with the frequency of the first clock signal CLK1.

As described above, the transmission device 10A according to the embodiment includes the oscillator 112 that oscillates the first clock signal CLK1 and the register signal reception unit 114 that receives the register signal Rs transmitted from the reception device 10B and used for controlling the first clock signal CLK1. The reception device 10B according to the embodiment includes the signal generation unit 134 that generates the register signal Rs for controlling the first clock signal CLK1 based on a comparison result obtained by comparing the reference clock signal INCK with one of the first clock signal CLK1 transmitted from the transmission device 10A and the second clock signal CLK2 which is based on the first clock signal CLK1 and the register signal transmission unit 135 that transmits the register signal Rs generated by the signal generation unit 134 to the transmission device 10A. The transceiver system 1 according to the embodiment includes the transmission device 10A and the reception device 10B according to the embodiment.

In the transmission device 10A, the reception device 10B, and the transceiver system 1 that have the configurations, only one kind of register signal Rs may be used as the control signal for controlling the first clock signal CLK1. On the other hand, in a transceiver system of the related art, three kinds of signals, the clock signal, a reference clock signal, and a serial digital interface (SDI) signal are necessary between a reception device and a transmission device in order to control a clock signal used to transmit and receive data between the transmission device and the reception device. Therefore, in the transmission device 10A, the reception device 10B, and the transceiver system 1 according to the embodiment, wirings between the transmission device 10A and the reception device 10B can be simplified, and thus miniaturization of the transmission device 10A can be achieved.

In the transmission device 10A, the number of terminals for the control signal for controlling the first clock signal CLK1 can be set to one (in the case of a differential signal, the number of terminals can be set to two). On the other hand, in a transmission device of the related art, three terminals for control signals for controlling the clock signal are necessary (six terminals are necessary in the case of the differential signal). Therefore, in the transmission device 10A, miniaturization of a semiconductor chip for forming the transmission unit 11 can be achieved. As a result, in the transmission device 10A, the reception device 10B, and the transceiver system 1 according to the embodiment, the miniaturization of the transmission device 10A can be achieved.

Further, in the transmission device 10A, the oscillator 112 is used to oscillate the first clock signal CLK1 rather than a PLL. As a result, in the transmission device 10A, the reception device 10B, and the transceiver system 1 according to the embodiment, the miniaturization of the transmission device 10A can be achieved.

Second Embodiment

A transmission device, a reception device, and a transceiver system according to a second embodiment of the present technology will be described with reference to FIGS. 5 to 7. First, schematic configurations of the transmission device, the reception device, and the transceiver system according to the embodiment will be described with reference to FIG. 5. The same reference numerals are given to constituent elements that have the same operations and functions as those of the transmission device, the reception device, and the transceiver system according to the foregoing first embodiment, and description thereof will be omitted.

In the transmission device, the reception device, and the transceiver system according to the embodiment, transmission data and a synchronization clock signal are transmitted and received in conformity with a clock-embedded scheme. As illustrated in FIG. 5, a transceiver system 2 according to the embodiment includes a transmission device 20A that transmits a predetermined signal and a reception device 20B that receives the predetermined signal transmitted from the transmission device 20A. The transceiver system 2 can be applied to, for example, an endoscope system and is configured such that the transmission device 20A transmits captured data captured by the transmission device 20A to the reception device 20B. The reception device 20B processes the captured data transmitted from the transmission device 20A and transmits the processed captured data to, for example, a display device (not illustrated). Therefore, miniaturization of the transmission device 20A is achieved so that the transmission device 20A can enter a narrow region such as the inside of a human body. The reception device 20B has a configuration in which a clock signal can be controlled to receive the captured data from the miniaturized transmission device 20A and to cause the transmission device 20A to stably operate.

The transmission device 20A according to the embodiment includes the data source 12 and a transmission unit 21 that transmits the data input from the data source 12 to an oscillator 112. In the embodiment, the transmission unit 21 and the data source 12 are formed in different semiconductor chips to be stacked. The transmission unit 21 and the data source 12 may be formed in the same semiconductor chip.

Figure 5:
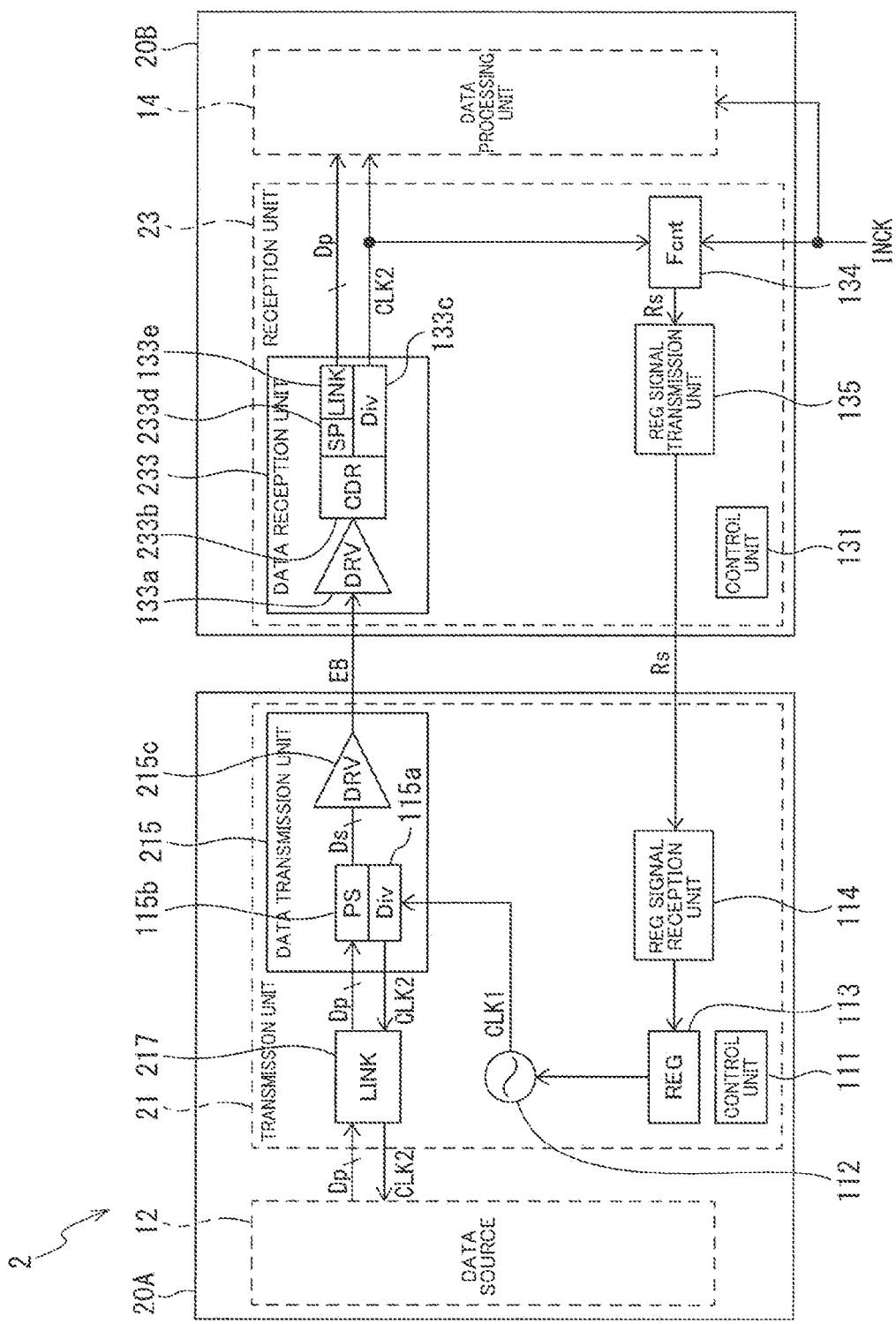
FIG. 5 is a functional block diagram illustrating a schematic configuration of a transmission device, a reception device, and a transceiver system according to a second embodiment of the present technology.
Figure 6:
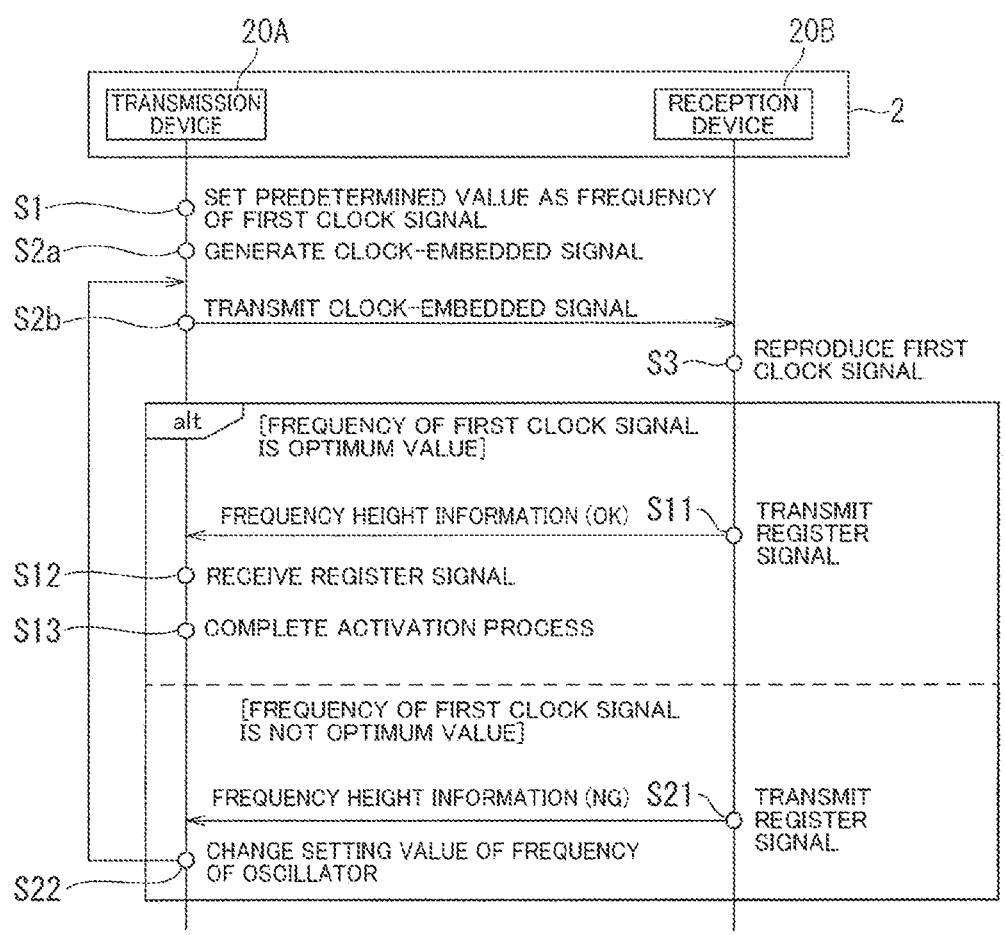
FIG. 6 is a sequence diagram (part 1) illustrating control of a frequency of a clock signal oscillated by the transmission device in the transceiver system according to the second embodiment of the present technology.

As illustrated in FIG. 5, the transmission unit 21 included in the transmission device 20A does not include a clock signal transmission unit to transmit the data Ds and the first clock signal CLK1 to the reception device 20B in conformity with the clock-embedded scheme. The transmission unit 21 includes a link unit 217 to which the data Dp is input from the data source 12. The transmission unit 21 includes a data transmission unit 215 that transmits a clock-embedded signal EB in which the first clock signal CLK1 is embedded in the data Ds to the reception device 20B. The reception device 20B corresponds to an example of an external device of the transmission device 20A. The data Ds in which the first clock signal CLK1 is embedded is data obtained by performing parallel-serial conversion on the data Dp output from the link unit 217.

The link unit 217 has a similar function as the link unit 117 of the foregoing first embodiment. Further, the link unit 217 has a function of converting the number of bits of the data Dp input from the data source 12. As an example of the clock-embedded scheme, 8B10B coding in which a clock signal is embedded in an 8-bit signal is known. For example, the link unit 217 may be configured to convert 8-bit data Dp into 10-bit data Dp so that 8B10B coding can be used in the embodiment. In the embodiment, as the coding for embedding a clock signal in data, not only 8B10B coding but also coding such as 64B66B, 128b130b, or 128b132b or another clock-embedded scheme may be used. In this case, the link unit 217 has a configuration in which a clock-embedded scheme to be used can be applied, so that transmission and reception of data between the transmission device 20A and the reception device 20B can be realized.

The data transmission unit 215 includes a divider 115a, a parallel-serial conversion unit 115b, and a driver 215c (which is an example of a transmission driving unit) that embeds the first clock signal CLK1 in the data Ds with a serial form synchronized with the first clock signal CLK1 and transmits the clock-embedded signal EB to the reception device 10B. The driver 215c embeds the first clock signal CLK1 of the single-ended mode in the data Ds of the single-ended mode input from the parallel-serial conversion unit 115b and generates the clock-embedded signal EB of the single-ended mode. The driver 215c outputs the generated clock-embedded signal EB to the reception device 20B. Thus, the transmission unit 21 can achieve a reduction of the number of pins (the number of terminals) used for input and output or the like. The driver 215c can perform input and output impedance conversion when the driver 215c has, for example, a configuration of a voltage follower. Therefore, since output impedance is lowered, the driver 215c can achieve an improvement in an output current. Thus, the transmission device 20A can inhibit an erroneous operation caused due to a decrease in a signal level of the clock-embedded signal EB (that is, a signal waveform of the clock-embedded signal EB becoming blunt) output from the driver 215c in a wiring connecting the transmission device 20A to the reception device 20B.

The driver 215c may convert the first clock signal CLK1 of the single-ended mode and the data Ds of the single-ended mode into a signal of a differential mode and embed the first clock signal CLK1 in the data Ds to generate the clock-embedded signal EB. In this case, the transmission unit 21 can transmit the clock-embedded signal EB at a low voltage although the number of pins (the number of terminals) used for input and output or the like is greater than in a case in which the clock-embedded signal EB of the single-ended mode is transmitted to the reception device 20B. The transmission device 20A can transmit the synchronized data Ds and first clock signal CLK1 to the reception device 20B compared to a case in which the data Ds and the first clock signal CLK1 are transmitted in a source synchronous scheme. Further, in the transmission device 20A, when the data Ds and the first clock signal CLK1 are transmitted in conformity with the clock-embedded scheme, a wiring for transmitting the first clock signal CLK1 is unnecessary compared to the source synchronous scheme. Thus, in the transceiver system 2, it is possible to achieve a reduction in the number of wirings between the transmission device 20A and the reception device 20B.

As illustrated in FIG. 5, a reception unit 23 included in the reception device 20B does not include a clock signal reception unit to receive the data Ds and the first clock signal CLK1 in conformity with the clock-embedded scheme. The reception unit 23 includes a data reception unit 233 including a reproduction unit 233b that reproduces the first clock signal CLK1 embedded in the data Ds and transmitted from the transmission device 20A from the data Ds. The transmission device 20A corresponds to an example of an external device of the reception device 20B.

The reproduction unit 233b has, for example, a clock data recovery (CDR) function. In FIG. 5 and other figures, a reproduction unit that has the CDR function is noted as "CDR". The reproduction unit 233b outputs the data Ds from which the first clock signal CLK1 is reproduced to the serial-parallel conversion unit 133d. The reproduction unit 233b outputs the first clock signal CLK1 reproduced from the data Ds to the divider 133c.

The data reception unit 233 includes a link unit 233e to which the data Dp of a parallel form output from the serial-parallel conversion unit 133d is input. The link unit 233e converts the data Dp output from the serial-parallel conversion unit 133d into a data form which can be processed by the data processing unit 14. Further, the link unit 233e changes the number of bits of the data Dp converted into the parallel form by the serial-parallel conversion unit 133d. For example, the link unit 233e may be configured to convert the number of bits of the data Dp input from the serial-parallel conversion unit 133d into the same number of bits as the data Dp output from the data source 12. For example, the link unit 233e may be configured to convert the number of bits of the data Dp input from the serial-parallel conversion unit 133d into the different number of bits from the data Dp output from the data source 12.

In this way, the data reception unit 233 can output the second clock signal CLK2 generated by dividing the frequency of the first clock signal CLK1 and the data Dp of the parallel form synchronized with the second clock signal CLK2 to the data processing unit 14. Further, the data reception unit 233 can output the second clock signal CLK2 to the signal generation unit 134.

The signal generation unit 134 can determine whether a difference between the frequency of the second clock signal CLK2 input from the data reception unit 233 and the frequency of the reference clock signal INCK input from the outside of the reception device 20B is within a predetermined error range and can generate the register signal Rs. Thus, the transmission device 20A, the reception device 20B, and the transceiver system 2 can control a deviation of the frequency of the first clock signal CLK1 as in the transmission device 10A, the reception device 10B, and the transceiver system 1 according to the foregoing first embodiment.

Next, a control process for the frequency of a clock signal in the transmission device 20A, the reception device 20B, and the transceiver system 2 according to the embodiment will be described with reference to FIGS. 6 and 7 in addition to FIG. 5. FIG. 6 is a sequence diagram illustrating a control process for the frequency of the clock signal performed during activation of the transceiver system 2. FIG. 7 is a sequence diagram illustrating a control process for the frequency of the clock signal performed during an operation after the activation of the transceiver system 2. In the embodiment, to facilitate understanding, a processing flow of the transceiver system 2 is divided into operations during activation and after the activation. However, in the processing flow of the transceiver system 2, a process in an operation after the activation continuously after end of the process during the activation may be, of course, performed. In the control process for the frequency of the clock signal according to the embodiment, the same reference numerals are given to similar processes to those of the control process for the frequency of the clock signal according to the foregoing first embodiment, and description thereof will be omitted.

(Step S2a)

In a step S2a subsequent to step S1, the transmission device 20A generates the clock-embedded signal EB, and the process proceeds to step S2b. In step S2a, the driver 215c of the data transmission unit 215 embeds the data Ds input from the parallel-serial conversion unit 115b and the first clock signal CLK1 of the single-ended mode input from the oscillator 112 in the data Ds of the single-ended mode under the control of the control unit 111. In this way, the driver 215c generates the clock-embedded signal EB of the single-ended mode.

(Step S2b)

In step S2b, the transmission device 20A outputs the clock-embedded signal EB to the reception device 20B. The data transmission unit 215 transmits the clock-embedded signal EB generated by the driver 215c to the reception device 20B under the control of the control unit 111.

(Step S3)

Continuously from step S2b, the transceiver system 2 performs a process of step S3, and the process proceeds to step S11 or S21 to perform the control process for the first clock signal CLK1 transmitted from the transmission device 20A to the reception device 20B. In step S3, the reception device 20B reproduces the first clock signal CLK1 from the clock-embedded signal EB transmitted from the transmission device 20A, and the process proceeds to step S11 or S21. In the data reception unit 233 of the reception device 20B, the reproduction unit 233b reproduces the first clock signal CLK1 from the clock-embedded signal EB transmitted from the transmission device 20A under the control of the control unit 131. After the process proceeds to step S11 or S21, the transceiver system 2 performs an operation similarly to the transceiver system 1 according to the foregoing first embodiment.

Subsequently, a process during operation after the activation of the transceiver system 2 (that is, during operation after the activation of the transmission device 20A and the reception device 20B), which is performed after the end of the process during activation of the transceiver system 2 (that is, during activation of the transmission device 20A and the reception device 20B) will be described with reference to FIG. 7.

(Step S102a)

Figure 7:
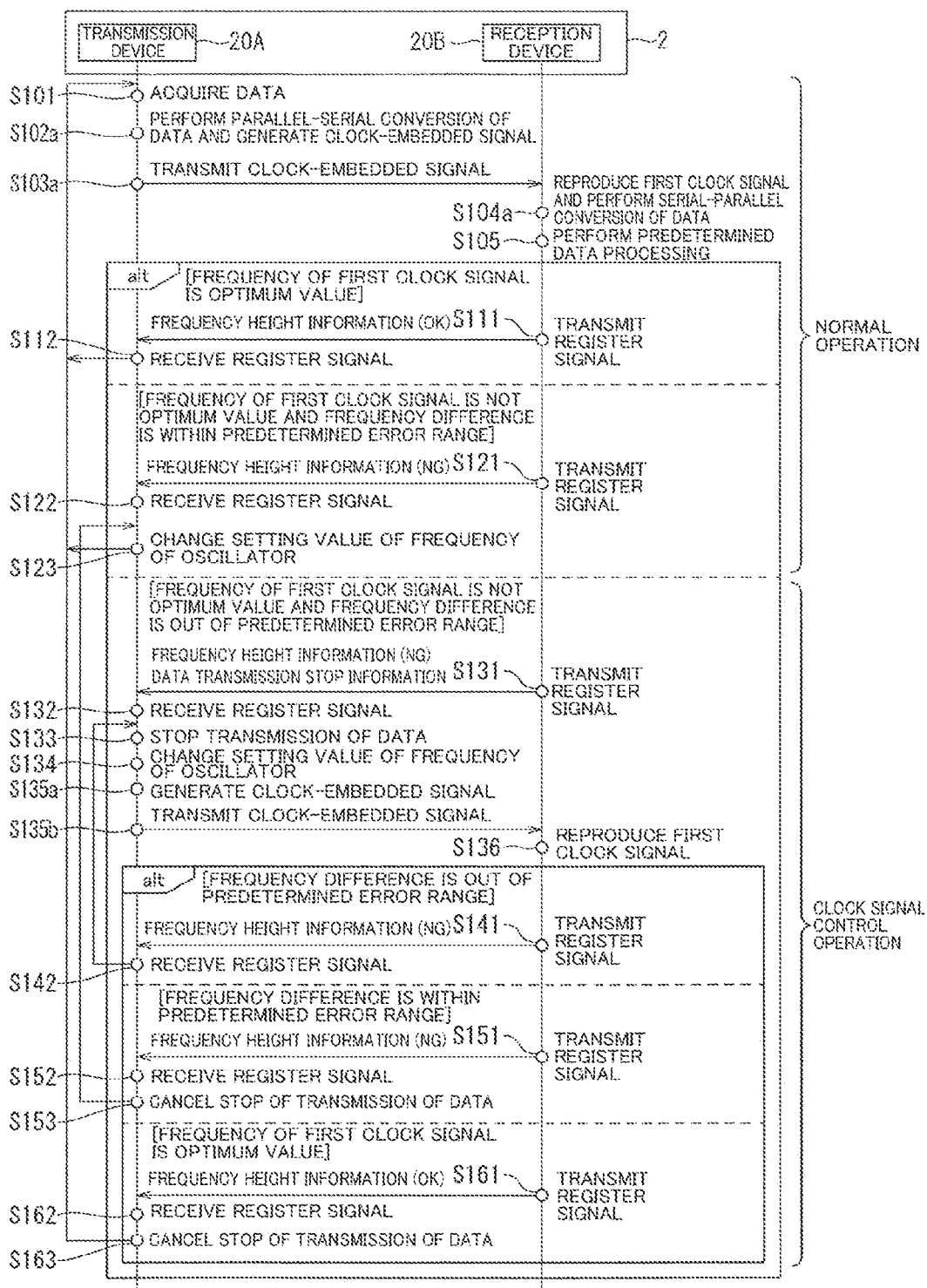
FIG. 7 is a sequence diagram (part 2) illustrating control of a frequency of a clock signal oscillated by the transmission device in the transceiver system according to the second embodiment of the present technology.

As illustrated in FIG. 7, in a step S102a subsequent to step S101, the transmission device 20A changes the data Dp of the parallel form into the data Ds of the serial form and generates the clock-embedded signal EB in which the first clock signal CLK1 is embedded in the data Ds, and the process proceeds to step S103a. The parallel-serial conversion unit 115b of the data transmission unit 115 outputs the data Ds synchronized with the first clock signal CLK1 input from the oscillator 112 to the driver 215c under the control of the control unit 111. The driver 215c embeds the data Ds input from the parallel-serial conversion unit 115b and the first clock signal CLK1 of the single-ended mode input from the oscillator 112 in the data Ds of the single-ended mode. In this way, the driver 215c generates the clock-embedded signal EB.

(Step S103a)

In step S103a, the transmission device 20A outputs the clock-embedded signal EB to the reception device 20B. The data transmission unit 215 transmits the clock-embedded signal EB generated by the driver 215c to the reception device 20B under the control of the control unit 111.

(Step S104a)

Continuously from step S103a, the transceiver system 2 performs a process of step S104a, and the process proceeds to step S105. As illustrated in FIG. 7, in step S104a, the reception device 20B reproduces the first clock signal CLK1 from the clock-embedded signal EB transmitted from the transmission device 20A and converts the data Ds of the serial form into the data Dp of the parallel form, and the process proceeds to step S105. In the data reception unit 233 of the reception device 20B, the reproduction unit 233b reproduces the first clock signal CLK1 from the clock-embedded signal EB transmitted from the transmission device 20A under the control of the control unit 131. In the data reception unit 233, the divider 133c divides the first clock signal CLK1 reproduced from the clock-embedded signal EB to generate the second clock signal CLK2 under the control of the control unit 131. In the data reception unit 233, the serial-parallel conversion unit 133d generates the data Dp of the parallel form synchronized with the second clock signal CLK2 generated by the divider 133c under the control of the control unit 131. In the data reception unit 233, the link unit 233e converts the number of bits of the data Dp input from the serial-parallel conversion unit 133d and converts the data into a data form which can be processed by the data processing unit 14 under the control of the control unit 131. Further, the data reception unit 233 outputs the data Dp synchronized with the second clock signal CLK2 to the data processing unit 14 and outputs the second clock signal CLK2 to the data processing unit 14 and the signal generation unit 134 under the control of the control unit 131.

(Step S135a)

As illustrated in FIG. 7, in step S135a subsequent to step S134, the transmission device 20A changes the data Dp of the parallel form into the data Ds of the serial form and embeds the first clock signal CLK1 with the changed frequency in the data Ds to generate the clock-embedded signal EB, and the process proceeds to step S135b. The parallel-serial conversion unit 115b of the data transmission unit 115 outputs the data Ds synchronized with the first clock signal CLK1 input from the oscillator 112 to the driver 215c under the control of the control unit 111. The driver 215c embeds the data Ds input from the parallel-serial conversion unit 115b and the first clock signal CLK1 of the single-ended mode input from the oscillator 112 in the data Ds of the single-ended mode. In this way, the driver 215c generates the clock-embedded signal EB.

(Step S135b)

In step S135b subsequent to step S135a, the transmission device 20A transmits the clock-embedded signal EB in which the first clock signal CLK1 with the changed frequency is embedded from the clock signal transmission unit 216 to the reception device 20B. In step S133 performed before step S135b, the transmission of the data is stopped. Therefore, since the data Dp is not input to the data transmission unit 215, only the first clock signal CLK1 is included in the clock-embedded signal EB output from the data transmission unit 215.

The reception device 20B can compare the frequency of the first clock signal CLK1 which is transmitted from the transmission device 20A and of which the frequency is changed with the frequency of the reference clock signal INCK and determine whether the frequency difference between the first clock signal CLK1 after the change in the frequency and the reference clock signal INCK is within the predetermined error range and whether the frequency of the first clock signal CLK1 is the optimum value.

As described above, the transmission device 20A according to the embodiment includes the oscillator 112 that oscillates the first clock signal CLK1 and the register signal reception unit 114 that receives the register signal Rs transmitted from the reception device 20B and used for controlling the first clock signal CLK1. The reception device 20B according to the embodiment includes the signal generation unit 134 that generates the register signal Rs for controlling the first clock signal CLK1 based on a comparison result obtained by comparing the reference clock signal INCK with one of the first clock signal CLK1 transmitted from the transmission device 20A and the second clock signal CLK2 which is based on the first clock signal CLK1 and the register signal transmission unit 135 that transmits the register signal Rs generated by the signal generation unit 134 to the transmission device 20A. The transceiver system 2 according to the embodiment includes the transmission device 20A and the reception device 20B according to the embodiment.

Thus, in the transmission device 20A, the reception device 20B, and the transceiver system 2 according to the embodiment, it is possible to obtain similar advantageous effects to those of the transmission device 10A, the reception device 10B, and the transceiver system 1 according to the foregoing first embodiment. In the transmission device 20A, the reception device 20B, and the transceiver system 2 according to the embodiment, a signal can be transmitted from the transmission device 20A to the reception device 20B in conformity with the clock-embedded scheme. Thus, in the transmission device 20A, the reception device 20B, and the transceiver system 2 according to the embodiment, it is possible to obtain the advantageous effect of synchronization between the first clock signal CLK1 and the data Ds compared to the transmission device 10A, the reception device 10B, and the transceiver system 1 according to the foregoing first embodiment.

In the transmission device 20A, the reception device 20B, and the transceiver system 2 according to the embodiment, wirings between the transmission device 20A and the reception device 20B can be simplified more than the transmission device 10A, the reception device 10B, and the transceiver system 1 according to the foregoing first embodiment, and thus further miniaturization of the transmission device 20A can be achieved.

Third Embodiment

A transmission device, a reception device, and a transceiver system according to a third embodiment of the present technology will be described with reference to FIG. 8. The same reference numerals are given to constituent elements that have the same operations and functions as those of the transmission device, the reception device, and the transceiver system according to the forgoing first embodiment, and description thereof will be omitted.

In the transmission device, the reception device, and the transceiver system according to the embodiment, transmission data and a synchronization clock signal are transmitted and received in conformity with a source synchronous scheme. Further, in the transmission device, the reception device, and the transceiver system according to the embodiment, bi-directional communication can be performed between the transmission device and the reception device.

Figure 8:
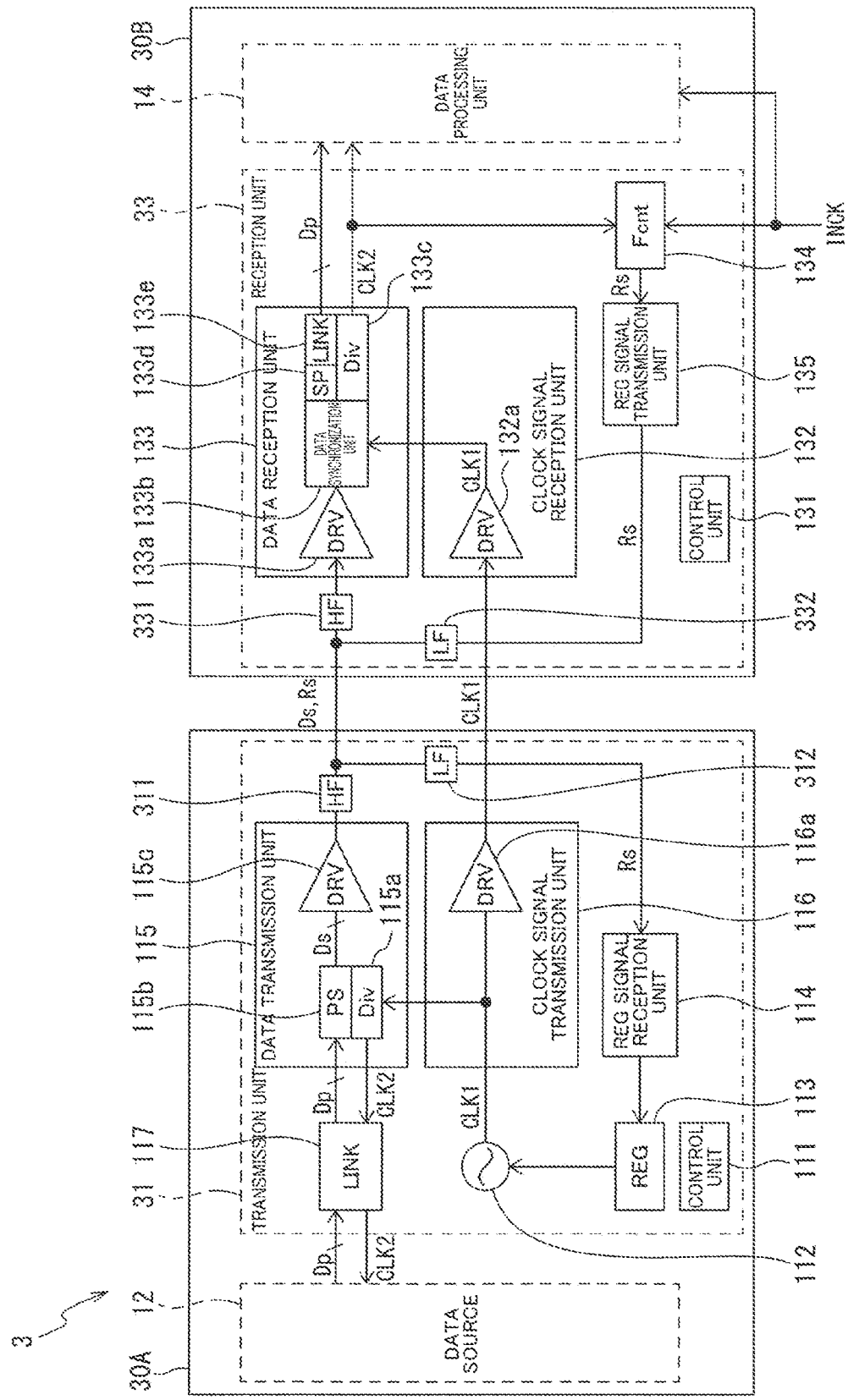
FIG. 8 is a functional block diagram illustrating a schematic configuration of a transmission device, a reception device, and a transceiver system according to a third embodiment of the present technology.

As illustrated in FIG. 8, a transceiver system 3 according to the embodiment includes a transmission device 30A that transmits a predetermined signal and a reception device 30B that receives the predetermined signal transmitted from the transmission device 30A. The transceiver system 3 can be applied to, for example, an endoscope system and is configured such that the transmission device 30A transmits captured data captured by the transmission device 30A to the reception device 30B. The reception device 30B processes the captured data transmitted from the transmission device 30A and transmits the processed captured data to, for example, a display device (not illustrated). Therefore, miniaturization of the transmission device 30A is achieved so that the transmission device 30A can enter a narrow region such as the inside of a human body. The reception device 30B has a configuration in which a clock signal can be controlled to receive the captured data from the miniaturized transmission device 30A and to cause the transmission device 30A to stably operate.

The transceiver system 3 is configured such that bi-directional communication can be performed between the transmission device 30A and the reception device 30B. Therefore, the data Ds transmitted from the transmission device 30A to the reception device 30B and the register signal Rs transmitted from the reception device 30B to the transmission device 30A are transmitted and received by a common wiring. The data Ds transmitted from the transmission device 30A to the reception device 30B and the register signal Rs transmitted from the reception device 30B to the transmission device 30A are set at different communication speeds. A communication speed of the data Ds is set to, for example, 1 Gbps and a communication speed of the register signal Rs is set to, for example, 1 Mbps.

The transmission device 30A includes reproduction units 311 and 312 that reproduce the data Ds and the register signals Rs transmitted and received via the common wiring. The reproduction unit 311 is connected between the common wiring by which the data Ds and the register signal Rs are transmitted and received (hereinafter referred to as a "common wiring") and an output terminal of the data transmission unit 115. The reproduction unit 312 is connected between the common wiring and an input terminal of the register signal reception unit 114.

The reproduction unit 311 is configured as, for example, a high-pass filter. In FIG. 8 and other figures, a reproduction unit that functions as the high-pass filter is noted as "HF". The reproduction unit 311 can pass the data Ds with a high frequency output from the data transmission unit 115 and can block the register signal Rs with a low frequency transmitted via the common wiring. Thus, the transmission device 30A can transmit the data Ds from the data transmission unit 115 to the reception device 30B and can inhibit an influence of the register signal Rs transmitted from the reception device 30B on the data transmission unit 115.

The reproduction unit 312 is configured as, for example, a low-pass filter. In FIG. 8 and other figures, a reproduction unit that functions as the low-pass filter is noted as "LF". The reproduction unit 312 can block the data Ds with a high frequency output from the data transmission unit 115 and can pass the register signal Rs with a low frequency transmitted via the common wiring. Thus, the transmission device 30A can inhibit the data Ds output from the data transmission unit 115 from being input to the register signal reception unit 114 and can input the register signal Rs transmitted from the reception device 30B to the register signal reception unit 114.

The reception device 30B includes reproduction units 331 and 332 that reproduce the data Ds and the register signal Rs transmitted and received via the common wiring. The reproduction unit 331 is connected between the common wiring and an input terminal of the data reception unit 133. The reproduction unit 332 is connected to the common wiring and an output terminal of the register signal transmission unit 135.

The reproduction unit 331 is configured as, for example, a high-pass filter. Therefore, the reproduction unit 331 can pass the data Ds with a high frequency transmitted from the transmission device 30A and can block the register signal Rs with a low frequency output from the register signal transmission unit 135. Thus, the reception device 30B can receive the data Ds transmitted from the data transmission unit 115 and can inhibit the register signal Rs output from the register signal transmission unit 135 from being input to the data reception unit 133.

The reproduction unit 332 is configured as, for example, a low-pass filter. Thus, the reproduction unit 332 can block the data Ds with a high frequency transmitted from the transmission device 30A and can pass the register signal Rs with a low frequency output from the register signal transmission unit 135. Thus, the reception device 30B can inhibit an influence of the data Ds transmitted from the transmission device 30A on the register signal transmission unit 135 and can transmit the register signal Rs output from the register signal transmission unit 135 to the transmission device 30A via the common wiring.

In the transmission device 30A, the reception device 30B, and the transceiver system 3, a full-duplex scheme of simultaneously transmitting and receiving the register signal Rs and the data Ds is used as the bi-directional communication. The transmission device 30A includes the reproduction units 311 and 312 and the reception device 30B includes the reproduction units 331 and 332. Therefore, in the transmission device 30A, the reception device 30B, and the transceiver system 3, the register signal Rs and the data Ds can be easily reproduced even when the full-duplex scheme is used.

In the transmission device 30A, the reception device 30B, and the transceiver system 3, a half-duplex scheme of transmitting the register signal Rs and the data Ds in a time division manner may be used as the bi-directional communication. In the half-duplex scheme, when a data signal acquired by the data source 12 is, for example, image data, the register signal Rs and the data Ds can be reproduced temporarily, for example, by transmitting the register signal Rs during a certain period of a blanking period. For example, since a vertical blanking period is longer than a horizontal blanking period, the register signal Rs may be transmitted in a certain period of the vertical blanking period of a communication speed. Since a communication speed of the data Ds is faster than that of the register signal Rs, the data Ds may be transmitted during at least one of the vertical blanking period and another predetermined period. Thus, it is possible to improve system efficiency for transmitting the register signal Rs and the data Ds. In the half-duplex scheme, it is not necessary to provide the reproduction units 311, 312, 331, and 332. Therefore, the transmission device 30A and the reception device 30B can be miniaturized and simplified.

As described above, the transmission device 30A according to the embodiment includes the oscillator 112 that oscillates the first clock signal CLK1 and the register signal reception unit 114 that receives the register signal Rs transmitted from the reception device 30B and used for controlling the first clock signal CLK1. The reception device 30B according to the embodiment includes the signal generation unit 134 that generates the register signal Rs for controlling the first clock signal CLK1 based on a comparison result obtained by comparing the reference clock signal INCK with one of the first clock signal CLK1 transmitted from the transmission device 30A and the second clock signal CLK2 which is based on the first clock signal CLK1 and the register signal transmission unit 135 that transmits the register signal Rs generated by the signal generation unit 134 to the transmission device 30A. The transceiver system 3 according to the embodiment includes the transmission device 30A and the reception device 30B according to the embodiment.

Thus, in the transmission device 30A, the reception device 30B, and the transceiver system 3 according to the embodiment, it is possible to obtain similar advantageous effects to those of the transmission device 10A, the reception device 10B, and the transceiver system 1 according to the foregoing first embodiment. In the transmission device 30A, the reception device 30B, and the transceiver system 3 according to the embodiment, the data Ds and the register signal Rs can be transmitted and received via the common wiring. Thus, in the transmission device 30A, the reception device 30B, and the transceiver system 3, it is possible to achieve a reduction in the number of wirings connecting the transmission device 30A to the reception device 30B than in the transmission device 10A, the reception device 10B, and the transceiver system 1 according to the foregoing first embodiment.

Fourth Embodiment

A transmission device, a reception device, and a transceiver system according to a fourth embodiment of the present technology will be described with reference to FIG. 9. The same reference numerals are given to constituent elements that have the same operations and functions as those of the transmission device, the reception device, and the transceiver system according to the forgoing first or second embodiment, and description thereof will be omitted.

In the transmission device, the reception device, and the transceiver system according to the embodiment, transmission data and a synchronization clock signal are transmitted and received in conformity with a clock-embedded scheme. Further, in the transmission device, the reception device, and the transceiver system according to the embodiment, bi-directional communication can be performed between the transmission device and the reception device.

Figure 9:
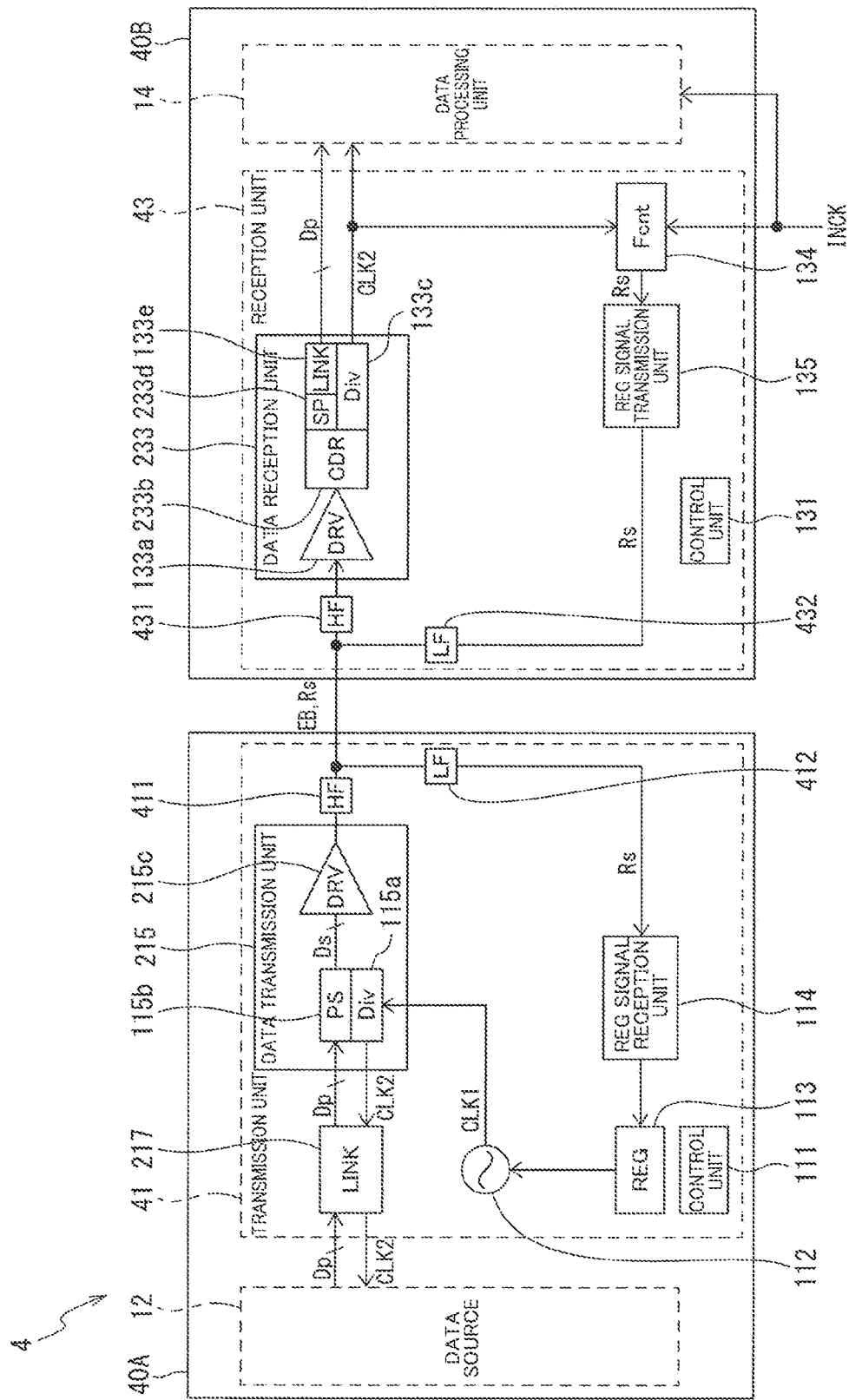
FIG. 9 is a functional block diagram illustrating a schematic configuration of a transmission device, a reception device, and a transceiver system according to a fourth embodiment of the present technology.

As illustrated in FIG. 9, a transceiver system 4 according to the embodiment includes a transmission device 40A that transmits a predetermined signal and a reception device 40B that receives the predetermined signal transmitted from the transmission device 40A. The transceiver system 4 can be applied to, for example, an endoscope system and is configured such that the transmission device 40A transmits captured data captured by the transmission device 40A to the reception device 40B. The reception device 40B processes the captured data transmitted from the transmission device 40A and transmits the processed captured data to, for example, a display device (not illustrated). Therefore, miniaturization of the transmission device 40A is achieved so that the transmission device 40A can enter a narrow region such as the inside of a human body. The reception device 40B has a configuration in which a clock signal can be controlled to receive the captured data from the miniaturized transmission device 40A and to cause the transmission device 40A to stably operate.

The transceiver system 4 is configured such that bi-directional communication can be performed between the transmission device 40A and the reception device 40B. Therefore, the clock-embedded signal EB transmitted from the transmission device 40A to the reception device 40B and the register signal Rs transmitted from the reception device 40B to the transmission device 40A are transmitted and received by a common wiring. The clock-embedded signal EB transmitted from the transmission device 40A to the reception device 40B and the register signal Rs transmitted from the reception device 40B to the transmission device 40A are set at different communication speeds. A communication speed of the clock-embedded signal EB is set to, for example, 1 Gbps and a communication speed of the register signal Rs is set to, for example, 1 Mbps.

The transmission device 40A includes reproduction units 411 and 412 that reproduce the clock-embedded signal EB and the register signals Rs transmitted and received via the common wiring. The reproduction unit 411 is connected between the common wiring by which the clock-embedded signal EB and the register signal Rs are transmitted and received (hereinafter referred to as a "common wiring") and an output terminal of the data transmission unit 115. The reproduction unit 412 is connected between the common wiring and an input terminal of the register signal reception unit 114.

The reproduction unit 411 is configured as, for example, a high-pass filter. The reproduction unit 411 can pass the clock-embedded signal EB with a high frequency output from the data transmission unit 115 and can block the register signal Rs with a low frequency transmitted via the common wiring. Thus, the transmission device 40A can transmit the clock-embedded signal EB from the data transmission unit 115 to the reception device 40B and can inhibit an influence of the register signal Rs transmitted from the reception device 40B on the data transmission unit 115.

The reproduction unit 412 is configured as, for example, a low-pass filter. The reproduction unit 412 can block the clock-embedded signal EB with a high frequency output from the data transmission unit 115 and can pass the register signal Rs with a low frequency transmitted via the common wiring. Thus, the transmission device 40A can inhibit the clock-embedded signal EB output from the data transmission unit 115 from being input to the register signal reception unit 114 and can input the register signal Rs transmitted from the reception device 40B to the register signal reception unit 114.

The reception device 40B includes reproduction units 431 and 432 that reproduce the clock-embedded signal EB and the register signal Rs transmitted and received via the common wiring. The reproduction unit 431 is connected between the common wiring and an input terminal of the data reception unit 233. The reproduction unit 432 is connected to the common wiring and an output terminal of the register signal transmission unit 135.

The reproduction unit 431 is configured as, for example, a high-pass filter. Therefore, the reproduction unit 431 can pass the clock-embedded signal EB with a high frequency transmitted from the transmission device 40A and can block the register signal Rs with a low frequency output from the register signal transmission unit 135. Thus, the reception device 40B can receive the clock-embedded signal EB transmitted from the data transmission unit 115 and can inhibit the register signal Rs output from the register signal transmission unit 135 from being input to the data reception unit 233.

The reproduction unit 432 is configured as, for example, a low-pass filter. Thus, the reproduction unit 432 can block the clock-embedded signal EB with a high frequency transmitted from the transmission device 40A and can pass the register signal Rs with a low frequency output from the register signal transmission unit 135. Thus, the reception device 40B can inhibit an influence of the clock-embedded signal EB transmitted from the transmission device 40A on the register signal transmission unit 135 and can transmit the register signal Rs output from the register signal transmission unit 135 to the transmission device 40A via the common wiring.

In the transmission device 40A, the reception device 40B, and the transceiver system 4, a full-duplex scheme of simultaneously transmitting and receiving the register signal Rs and the clock-embedded signal EB is used as the bi-directional communication. The transmission device 40A includes the reproduction units 411 and 412 and the reception device 40B includes the reproduction units 431 and 432. Therefore, in the transmission device 40A, the reception device 40B, and the transceiver system 4, the register signal Rs and the clock-embedded signal EB can be easily reproduced even when the full-duplex scheme is used.

In the transmission device 40A, the reception device 40B, and the transceiver system 4, a half-duplex scheme of transmitting the register signal Rs and the clock-embedded signal EB in a time division manner may be used as the bi-directional communication. In the half-duplex scheme, when a data signal acquired by the data source 12 is, for example, image data, the register signal Rs and the clock-embedded signal EB can be reproduced temporarily, for example, by transmitting the register signal Rs during a certain period of a blanking period. For example, the register signal Rs of which the communication speed is slower may be transmitted in a vertical blanking period. Since a communication speed of the data Ds is faster than that of the register signal Rs, the data Ds may be transmitted during at least one of the vertical blanking period and another predetermined period. Thus, it is possible to improve system efficiency for transmitting the register signal Rs and the clock-embedded signal EB. In the half-duplex scheme, it is not necessary to provide the reproduction units 411, 412, 431, and 432. Therefore, the transmission device 40A and the reception device 40B can be miniaturized and simplified.

As described above, the transmission device 40A according to the embodiment includes the oscillator 112 that oscillates the first clock signal CLK1 and the register signal reception unit 114 that receives the register signal Rs transmitted from the reception device 40B and used for controlling the first clock signal CLK1. The reception device 40B according to the embodiment includes the signal generation unit 134 that generates the register signal Rs for controlling the first clock signal CLK1 based on a comparison result obtained by comparing the reference clock signal INCK with one of the first clock signal CLK1 transmitted from the transmission device 40A and the second clock signal CLK2 which is based on the first clock signal CLK1 and the register signal transmission unit 135 that transmits the register signal Rs generated by the signal generation unit 134 to the transmission device 40A. The transceiver system 4 according to the embodiment includes the transmission device 40A and the reception device 40B according to the embodiment.

Thus, in the transmission device 40A, the reception device 40B, and the transceiver system 4 according to the embodiment, it is possible to obtain similar advantageous effects to those of the transmission device 10A, the reception device 10B, and the transceiver system 1 according to the foregoing first embodiment. In the transmission device 40A, the reception device 40B, and the transceiver system 4 according to the embodiment, the clock-embedded signal EB and the register signal Rs can be transmitted and received via the common wiring. Thus, it is possible to achieve a reduction in the number of wirings connecting the transmission device 40A to the reception device 40B.

Fifth Embodiment

A transmission device, a reception device, and a transceiver system according to a fifth embodiment of the present technology will be described with reference to FIG. 10. The same reference numerals are given to constituent elements that have the same operations and functions as those of the transmission device, the reception device, and the transceiver system according to the forgoing first or second embodiment, and description thereof will be omitted.

In the transmission device, the reception device, and the transceiver system according to the embodiment, transmission data and a synchronization clock signal are transmitted and received in conformity with a synchronous scheme. Further, in the transmission device, the reception device, and the transceiver system according to the embodiment, a plurality of data transmission units and a plurality of data reception units may be included.

Figure 10:
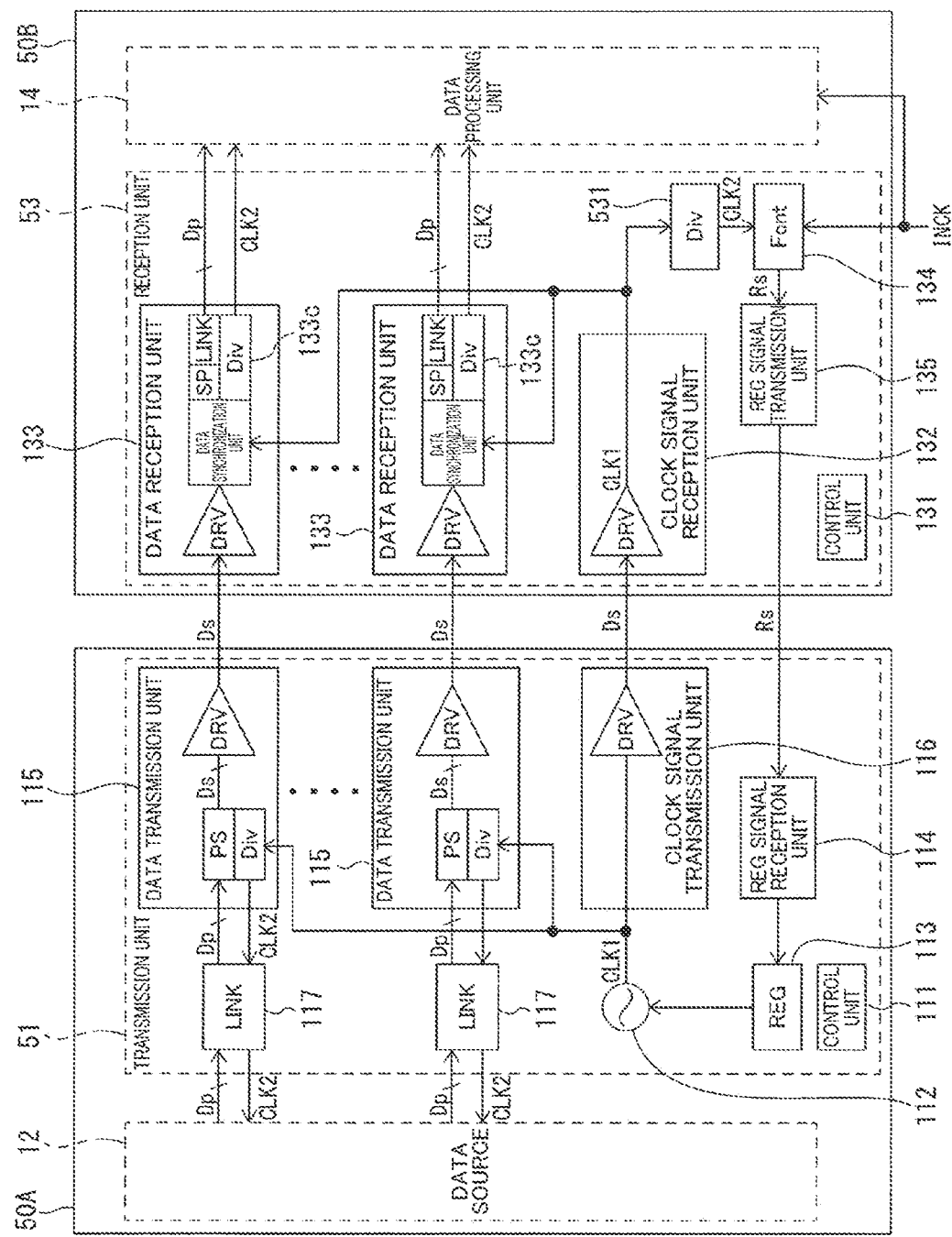
FIG. 10 is a functional block diagram illustrating a schematic configuration of a transmission device, a reception device, and a transceiver system according to a fifth embodiment of the present technology.

As illustrated in FIG. 10, a transceiver system 5 according to the embodiment includes a transmission device 50A that transmits a predetermined signal and a reception device 50B that receives the predetermined signal transmitted from the transmission device 50A. The transceiver system 5 can be applied to, for example, an endoscope system and is configured such that the transmission device 50A transmits captured data captured by the transmission device 50A to the reception device 50B. The reception device 50B processes the captured data transmitted from the transmission device 50A and transmits the processed captured data to, for example, a display device (not illustrated). Therefore, miniaturization of the transmission device 50A is achieved so that the transmission device 50A can enter a narrow region such as the inside of a human body. The reception device 50B has a configuration in which a clock signal can be controlled to receive the captured data from the miniaturized transmission device 50A and to cause the transmission device 50A to stably operate.

A transmission unit 51 included in the transmission device 50A includes a plurality of data transmission units 115 (two data transmission units are illustrated in FIG. 10). Each of the plurality of data transmission units 115 has the same configuration as the data transmission unit 115 in the foregoing first embodiment and has the same function.

A reception unit 53 included in the reception device 50B includes a plurality of data reception units 133 (two data reception units are illustrated in FIG. 10). Each of the plurality of data reception units 133 has the same configuration as the data reception unit 133 in the foregoing first embodiment and has the same function. The reception unit 53 has the same number of data reception units 133 as the number of data transmission units 115 provided in the transmission unit 51. The data transmission units 115 and the data reception units 133 are connected to have a one-to-one relationship.

The reception unit 53 includes a divider 531 provided between the clock signal reception unit 132 and the signal generation unit 134. The divider 531 divides the first clock signal CLK1 output from the clock signal reception unit 132 to generate the second clock signal CLK2. The divider 531 and each divider 133c provided in the plurality of data reception units 133 generate the second clock signal CLK2 with the same frequency. Thus, the reception unit 53 can control the frequency of the first clock signal CLK1 even when the second clock signal CLK2 output from the data reception unit 133 is not used.

As described above, the transmission device 50A according to the embodiment includes the oscillator 112 that oscillates the first clock signal CLK1 and the register signal reception unit 114 that receives the register signal Rs transmitted from the reception device 50B and used for controlling the first clock signal CLK1. The reception device 50B according to the embodiment includes the signal generation unit 134 that generates the register signal Rs for controlling the first clock signal CLK1 based on a comparison result obtained by comparing the reference clock signal INCK with one of the first clock signal CLK1 transmitted from the transmission device 50A and the second clock signal CLK2 which is based on the first clock signal CLK1 and the register signal transmission unit 135 that transmits the register signal Rs generated by the signal generation unit 134 to the transmission device 50A. The transceiver system 5 according to the embodiment includes the transmission device 50A and the reception device 50B according to the embodiment.

Thus, in the transmission device 50A, the reception device 50B, and the transceiver system 5 according to the embodiment, it is possible to obtain similar advantageous effects to those of the transmission device 10A, the reception device 10B, and the transceiver system 1 according to the foregoing first embodiment.

Sixth Embodiment

A transmission device, a reception device, and a transceiver system according to a sixth embodiment of the present technology will be described with reference to FIG. 11. The same reference numerals are given to constituent elements that have the same operations and functions as those of the transmission device, the reception device, and the transceiver system according to the forgoing first or second embodiment, and description thereof will be omitted.

In the transmission device, the reception device, and the transceiver system according to the embodiment, transmission data and a synchronization clock signal are transmitted and received in conformity with a clock-embedded scheme. Further, in the transmission device, the reception device, and the transceiver system according to the embodiment, the plurality of data transmission units are included and the plurality of data reception units are included.

Figure 11:
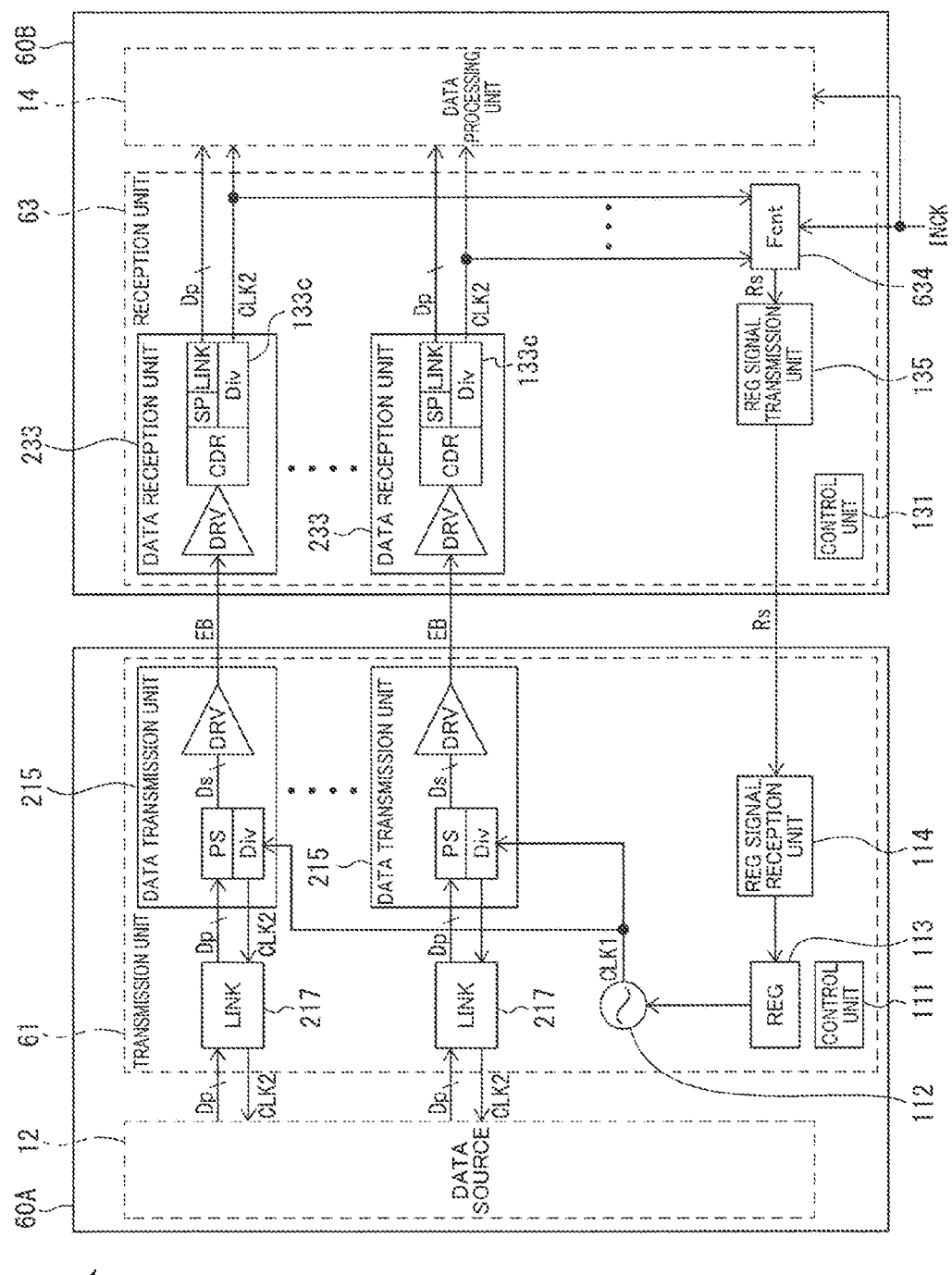
FIG. 11 is a functional block diagram illustrating a schematic configuration of a transmission device, a reception device, and a transceiver system according to a sixth embodiment of the present technology.

As illustrated in FIG. 11, a transceiver system 6 according to the embodiment includes a transmission device 60A that transmits a predetermined signal and a reception device 60B that receives the predetermined signal transmitted from the transmission device 60A. The transceiver system 6 can be applied to, for example, an endoscope system and is configured such that the transmission device 60A transmits captured data captured by the transmission device 60A to the reception device 60B. The reception device 60B processes the captured data transmitted from the transmission device 60A and transmits the processed captured data to, for example, a display device (not illustrated). Therefore, miniaturization of the transmission device 60A is achieved so that the transmission device 60A can enter a narrow region such as the inside of a human body. The reception device 60B has a configuration in which a clock signal can be controlled to receive the captured data from the miniaturized transmission device 60A and to cause the transmission device 60A to stably operate.

A transmission unit 61 included in the transmission device 60A includes a plurality of data transmission units 215 (two data transmission units are illustrated in FIG. 11). Each of the plurality of data transmission units 215 has the same configuration as the data transmission unit 215 in the foregoing second embodiment and has the same function.

A reception unit 63 included in the reception device 60B includes a plurality of data reception units 233 (two data reception units are illustrated in FIG. 10). Each of the plurality of data reception units 233 has the same configuration as the data reception unit 233 in the foregoing second embodiment and has the same function. The reception unit 63 has the same number of data reception units 233 as the number of data transmission units 215 provided in the transmission unit 61. The data transmission units 215 and the data reception units 233 are connected to have a one-to-one relationship.

The second clock signal CLK2 output from each of the plurality of data reception units 233 is input to a signal generation unit 634 included in the reception unit 63. The signal generation unit 634 compares the reference clock signal INCK with all the plurality of second clock signals CLK2 input from the plurality of data reception units 233. Thus, the signal generation unit 634 can control the first clock signal CLK1 by comparing the reference clock signal INCK with the second clock signals CLK2 even when transmission of the first clock signal CLK1 in one of the plurality of data transmission units 215 and the plurality of data reception units 233 fails. The signal generation unit 634 may be configured to compare the reference clock signal INCK with one of the plurality of second clock signals CLK2.

As described above, the transmission device 60A according to the embodiment includes the oscillator 112 that oscillates the first clock signal CLK1 and the register signal reception unit 114 that receives the register signal Rs transmitted from the reception device 60B and used for controlling the first clock signal CLK1. The reception device 60B according to the embodiment includes the signal generation unit 634 that generates the register signal Rs for controlling the first clock signal CLK1 based on a comparison result obtained by comparing the reference clock signal INCK with one of the first clock signal CLK1 transmitted from the transmission device 60A and the second clock signal CLK2 which is based on the first clock signal CLK1 and the register signal transmission unit 135 that transmits the register signal Rs generated by the signal generation unit 634 to the transmission device 60A. The transceiver system 6 according to the embodiment includes the transmission device 60A and the reception device 60B according to the embodiment.

Thus, in the transmission device 60A, the reception device 60B, and the transceiver system 6 according to the embodiment, it is possible to obtain similar advantageous effects to those of the transmission device 20A, the reception device 20B, and the transceiver system 2 according to the foregoing second embodiment.

Seventh Embodiment

A transmission device, a reception device, and a transceiver system according to a seventh embodiment of the present technology will be described with reference to FIG. 12. The same reference numerals are given to constituent elements that have the same operations and functions as those of the transmission device, the reception device, and the transceiver system according to the forgoing first, second, or sixth embodiment, and description thereof will be omitted.

In the transmission device, the reception device, and the transceiver system according to the embodiment, transmission data and a synchronization clock signal are transmitted and received in conformity with a clock-embedded scheme. Further, in the transmission device, the reception device, and the transceiver system according to the embodiment, a plurality of data transmission units and a plurality of data reception units may be included. Further, in the transmission device, the reception device, and the transceiver system according to the embodiment, the frequency of the second clock signal generated in the plurality of data transmission units can be changed for each data transmission unit.

Figure 12:
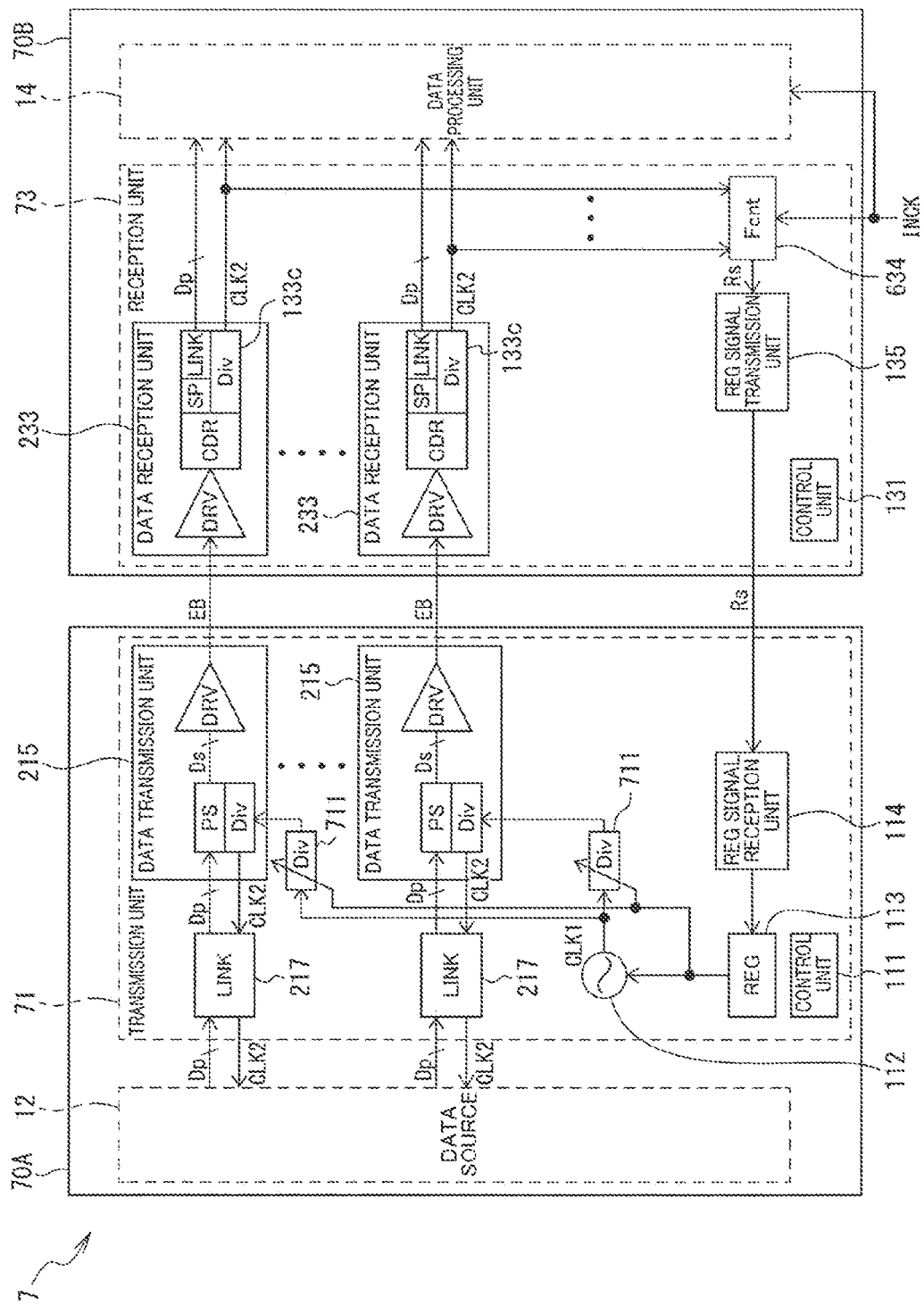
FIG. 12 is a functional block diagram illustrating a schematic configuration of a transmission device, a reception device, and a transceiver system according to a seventh embodiment of the present technology.

As illustrated in FIG. 12, a transceiver system 7 according to the embodiment includes a transmission device 70A that transmits a predetermined signal and a reception device 70B that receives the predetermined signal transmitted from the transmission device 70A. The transceiver system 7 can be applied to, for example, an endoscope system and is configured such that the transmission device 70A transmits captured data captured by the transmission device 70A to the reception device 70B. The reception device 70B processes the captured data transmitted from the transmission device 70A and transmits the processed captured data to, for example, a display device (not illustrated). Therefore, miniaturization of the transmission device 70A is achieved so that the transmission device 70A can enter a narrow region such as the inside of a human body. The reception device 70B has a configuration in which a clock signal can be controlled to receive the captured data from the miniaturized transmission device 70A and to cause the transmission device 70A to stably operate.

A transmission unit 71 included in the transmission device 70A includes a plurality of data transmission units 215 (two data transmission units are illustrated in FIG. 12). Each of the plurality of data transmission units 215 has the same configuration as the data transmission unit 215 in the foregoing second embodiment and has the same function.

The transmission unit 71 includes a divider 711 provided between the oscillator 112 and the divider 115a of the data transmission unit 215. The transmission unit 71 includes the same number of dividers 711 as the number of data transmission units 215. The first clock signal CLK1 is input to the divider 711. The divider 711 changes the number of times the first clock signal CLK1 is divided. Thus, the transmission unit 71 can change the frequency of the second clock signal CLK2 generated by the divider 115a in each data transmission unit 215.

A setting value of the number of times the first clock signal CLK1 is divided by the divider 711 is stored in the register 113.

As described above, the transmission device 70A according to the embodiment includes the oscillator 112 that oscillates the first clock signal CLK1 and the register signal reception unit 114 that receives the register signal Rs transmitted from the reception device 70B and used for controlling the first clock signal CLK1. The reception device 70B according to the embodiment includes the signal generation unit 634 that generates the register signal Rs for controlling the first clock signal CLK1 based on a comparison result obtained by comparing the reference clock signal INCK with one of the first clock signal CLK1 transmitted from the transmission device 70A and the second clock signal CLK2 which is based on the first clock signal CLK1 and the register signal transmission unit 135 that transmits the register signal Rs generated by the signal generation unit 634 to the transmission device 70A. The transceiver system 7 according to the embodiment includes the transmission device 70A and the reception device 70B according to the embodiment.

Thus, in the transmission device 70A, the reception device 70B, and the transceiver system 7 according to the embodiment, it is possible to obtain similar advantageous effects to those of the transmission device 60A, the reception device 60B, and the transceiver system 6 according to the foregoing sixth embodiment.

In the transmission device 70A, the reception device 70B, and the transceiver system 7 according to the embodiment, the frequency of the first clock signal CLK1 input to each divider 115a of the plurality of data transmission units 215 can be changed. Therefore, in the transmission device 70A, the reception device 70B, and the transceiver system 7 according to the embodiment, the frequency of the first clock signal CLK1 controlled from the reception device 70B can be changed in accordance with a process condition of the transmission unit 71, a power condition of the transmission device 70A, an ambient temperature condition of the transmission device 70A, or the like. Thus, in the embodiment, by appropriately controlling the transmission device 70A, it is possible to operate the transceiver system 7 stably and efficiently. In the embodiment, by detecting load situations of every plurality of data transmission units 215 and every plurality of data reception units 233 (each lane) and changing a data rate for each lane, it is possible to efficiently operate the transceiver system 7.

Eighth Embodiment

A transmission device, a reception device, and a transceiver system according to an eighth embodiment of the present technology will be described with reference to FIG. 13. The same reference numerals are given to constituent elements that have the same operations and functions as those of the transmission device, the reception device, and the transceiver system according to the forgoing first embodiment, and description thereof will be omitted.

In the transmission device, the reception device, and the transceiver system according to the embodiment, transmission data and a synchronization clock signal are transmitted and received in conformity with a source synchronous scheme.

Figure 13:
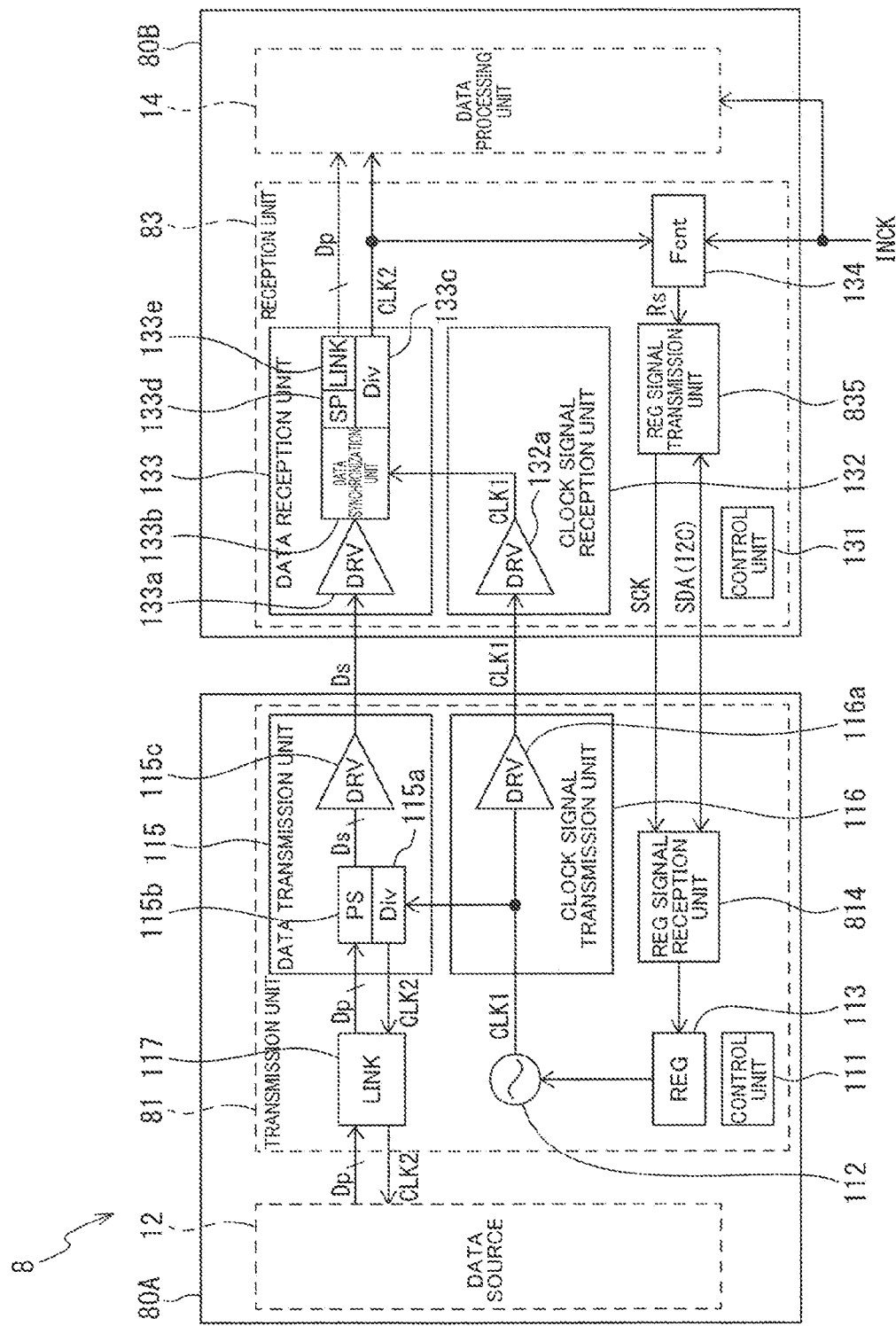
FIG. 13 is a functional block diagram illustrating a schematic configuration of a transmission device, a reception device, and a transceiver system according to an eighth embodiment of the present technology.

As illustrated in FIG. 13, a transceiver system 8 according to the embodiment includes a transmission device 80A that transmits a predetermined signal and a reception device 80B that receives the predetermined signal transmitted from the transmission device 80A. The transceiver system 8 can be applied to, for example, an endoscope system and is configured such that the transmission device 80A transmits captured data captured by the transmission device 80A to the reception device 80B. The reception device 80B processes the captured data transmitted from the transmission device 80A and transmits the processed captured data to, for example, a display device (not illustrated). Therefore, miniaturization of the transmission device 80A is achieved so that the transmission device 80A can enter a narrow region such as the inside of a human body. The reception device 80B has a configuration in which a clock signal can be controlled to receive the captured data from the miniaturized transmission device 80A and to cause the transmission device 80A to stably operate.

A serial clock signal SCK and SDA signal of the I2C standard are transmitted and received between a register signal reception unit 814 included in the transmission device 80A and a register signal transmission unit 835 included in the reception device 80B. SPI, UART, or the like which is another serial transmission standard may be used between the register signal reception unit 814 and the register signal transmission unit 835. The register signal transmission unit 835 generates the serial clock signal SCK and SDI signal based on the register signal Rs generated by the signal generation unit 134. Therefore, in the embodiment, it is not necessary to transmit and receive the reference clock signal INCK between the transmission device 80A and the reception device 80B. Thus, in the transceiver system 8 according to the embodiment, it is possible to reduce the number of control signals for controlling the synchronization clock signal compared to a transceiver system of the related art.

As described above, the transmission device 80A according to the embodiment includes the oscillator 112 that oscillates the first clock signal CLK1 and the register signal reception unit 814 that receives the serial clock signal SCK and SDI signal transmitted from the reception device 80B and used for controlling the first clock signal CLK1. The reception device 80B according to the embodiment includes the signal generation unit 134 that generates the register signal Rs for controlling the first clock signal CLK1 based on a comparison result obtained by comparing the reference clock signal INCK with one of the first clock signal CLK1 transmitted from the transmission device 80A and the second clock signal CLK2 which is based on the first clock signal CLK1 and the register signal transmission unit 835 that transmits the serial clock signal SCK and SDI signal which are based on the register signal Rs generated by the signal generation unit 134 to the transmission device 80A. The transceiver system 8 according to the embodiment includes the transmission device 80A and the reception device 80B according to the embodiment.

Thus, in the transmission device 80A, the reception device 80B, and the transceiver system 8 according to the embodiment, it is possible to obtain similar advantageous effects to those of the transmission device 80A, the reception device 80B, and the transceiver system 8 according to the foregoing first embodiment.

The present technology is not limited to the foregoing embodiments and can be modified in various forms. The reception device may separately include a divider that has the same configuration as the divider provided in the data reception unit and the signal generation unit may be configured to compare the reference clock signal with the second clock signal output from this divider.

The signal generation unit may be configured to compare the reference clock signal with the first clock signal input from the transmission device. The reference clock signal in this case is a signal with a higher frequency than the frequency of the reference clock signal in the case of the comparison with the second clock signal.

The reception device includes the driver in the input unit of the data Ds and the first clock signal, but the present technology is not limited thereto. The reception device may include an equalizer in the input unit of the data Ds or the first clock signal. For example, when the transceiver system is applied to an endoscope system, a wiring connecting the transmission device to the reception device is long. Therefore, various signals transmitted from the transmission device to the reception device may be attenuated in some cases. When the reception device includes an equalizer in the input unit, the equalizer can amplify the attenuated various signals as necessary. Thus, the reception device can achieve an improvement in reproduction of data acquired by the transmission device.

The register signal may include various kinds of information as well as the frequency height information for controlling the frequency of the first clock signal. For example, the register signal may be used for a different purpose from the control of the frequency of the first clock signal, such as information regarding various setting values stored in a register (for example, a data rate of each lane, information for adjusting an output amplitude of DRV, or the like).

The transmission device, the reception device, and the transceiver system according to the fifth to seventh embodiments may be configured to be able to perform bi-directional communication. In the transmission device, the reception device, and the transceiver system according to the fifth to seventh embodiments, both the plurality of data transmission units and the plurality of data reception units may be configured to be able to perform the bi-directional communication or some of the plurality of data transmission units and the plurality of data reception units may be configured to be able to perform the bi-directional communication.

The technology according to the present disclosure can be applied to the foregoing transmission device, reception device, and transceiver system.

<Application Example to In-Vivo Information Acquisition System>

The technology according to the present disclosure (the present technology) can be applied to various products. For example, the technology according to the present disclosure may be applied to an endoscopic surgery system.

Figure 14:
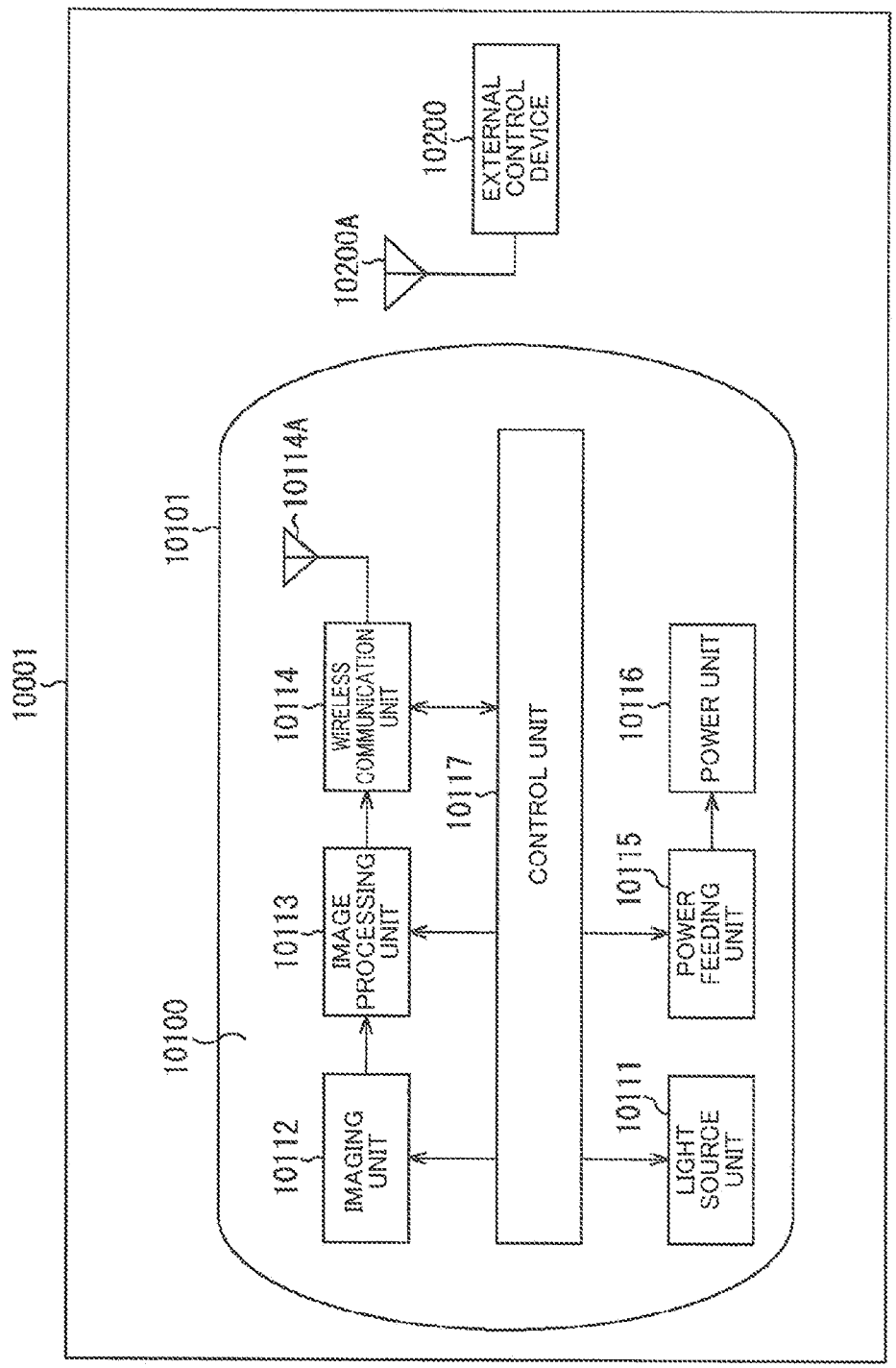
FIG. 14 is a block diagram illustrating an example of a schematic configuration of an in-vivo information acquisition system.

FIG. 14 is a block diagram illustrating an example of a schematic configuration of an in-vivo information acquisition system to which the technology according to the present disclosure (the present technology) can be applied and which is used for a patient who uses a capsule type endoscope.

An in-vivo information acquisition system 10001 includes a capsule type endoscope 10100 and an external control device 10200.

In an examination, the capsule type endoscope 10100 is swallowed by a patient. The capsule type endoscope 10100 has an imaging function and a wireless communication function, sequentially captures images of the insides of organs such as a stomach or intestines (hereinafter referred to as in-vivo images) at a predetermined interval while moving by peristalsis or the like inside the organs, and sequentially transmits information regarding the in-vivo images wirelessly to the external control device 10200 outside the body until the capsule type endoscope 10100 is excreted spontaneously from the patient.

The external control device 10200 generally controls an operation of the in-vivo information acquisition system 10001. The external control device 10200 receives the information regarding the in-vivo images transmitted from the capsule type endoscope 10100 and generates image data to display the in-vivo images on a display device (not illustrated) based on the information regarding the received in-vivo images.

In the in-vivo information acquisition system 10001, in this way, the in-vivo images obtained by imaging in-vivo states of the patient can be obtained frequently when the capsule type endoscope 10100 is swallowed and excreted.

The configurations and functions of the capsule type endoscope 10100 and the external control device 10200 will be described in more detail.

The capsule type endoscope 10100 includes a capsule type casing 10101. A light source unit 10111, an imaging unit 10112, an image processing unit 10113, a wireless communication unit 10114, a power feeding unit 10115, a power unit 10116, and a control unit 10117 are contained inside the casing 10101.

The light source unit 10111 includes, for example, a light source such as a light-emitting diode (LED) and radiates light toward an imaging visual field of the imaging unit 10112.

The imaging unit 10112 includes an image sensor and an optical system formed by a plurality of lenses provided in the front of the image sensor. Reflected light of the light radiated to a body tissue which is an examination target (hereinafter referred to as examination light) is condensed by the optical system to be incident on the image sensor. In the imaging unit 10112, the examination light incident on the image sensor is photoelectrically converted and an image signal corresponding to the examination light is generated. The image signal generated by the imaging unit 10112 is supplied to the image processing unit 10113.

The image processing unit 10113 includes a processor such as a central processing unit (CPU) or a graphics processing unit (GPU) and performs various kinds of signal processing on the image signal generated by the imaging unit 10112. The image processing unit 10113 supplies the image signal subjected to the signal processing as raw data to the wireless communication unit 10114.

The wireless communication unit 10114 performs a predetermined process such as a modulation process on the image signal on which the image processing unit 10113 performs the signal processing and transmits the image signal to the external control device 10200 via an antenna 10114A. The wireless communication unit 10114 receives a control signal related to driving control of the capsule type endoscope 10100 from the external control device 10200 via the antenna 10114A. The wireless communication unit 10114 supplies the control signal received from the external control device 10200 to the control unit 10117.

The power feeding unit 10115 includes a power receiving antenna coil, a power regeneration circuit, and the like, that regenerates power from a current generated in the antenna coil, and a boosting circuit. In the power feeding unit 10115, power is generated using a so-called contactless charging principle.

The power unit 10116 includes a secondary battery and charges power generated by the power feeding unit 10115. In FIG. 1001, to avoid the complicated figure, an arrow or the like indicating a supply destination of power from the power unit 10116 is not illustrated. However, power stored in the power unit 10116 can be supplied to the light source unit 10111, the imaging unit 10112, the image processing unit 10113, the wireless communication unit 10114, and the control unit 10117 and used to drive them.

The control unit 10117 includes a processor such as a CPU and appropriately controls the driving of the light source unit 10111, the imaging unit 10112, the image processing unit 10113, the wireless communication unit 10114, and the power feeding unit 10115 in accordance with control signals transmitted from the external control device 10200.

The external control device 10200 includes a processor such as a CPU or a GPU, or a microcomputer or a control substrate in which a processor and a storage element such as a memory are consolidated. The external control device 10200 controls an operation of the capsule type endoscope 10100 by transmitting a control signal to the control unit 10117 of the capsule type endoscope 10100 via the antenna 10200A. In the capsule type endoscope 10100, for example, a radiation condition of light to an examination target in the light source unit 10111 can be changed in accordance with a control signal from the external control device 10200. An imaging condition (for example, a frame rate, an exposure value, and the like in the imaging unit 10112) can be changed in accordance with a control signal from the external control device 10200. Content of a process in the image processing unit 10113 or conditions that the wireless communication unit 10114 transmits an image signal (for example, a transmission interval, the number of images to be transmitted, and the like) may be changed in accordance with a control signal from the external control device 10200.

The external control device 10200 performs various kinds of image processing on the image signal transmitted from the capsule type endoscope 10100 to generate image data for displaying the captured in-vivo images on the display device. As the image processing, for example, various kinds of signal processing such as a development process (demosaic processing), an image improving process (a bandwidth enhancement process, super-resolution processing, a noise reduction (NR) process, and/or a camera-shake correction process), and/or an enlargement process (electronic zoom processing) can be performed. The external control device 10200 controls driving of the display device such that captured in-vivo images are displayed based on the generated image data. Alternatively, the external control device 10200 may cause a recording device (not illustrated) to record the generated image data or may cause a printing device (not illustrated) to print and output the generated image data.

The example of the in-vivo information acquisition system to which the technology according to the present disclosure can be applied will be described. The technology according to the present disclosure can be used for an interface between the imaging unit 10112 and the image processing unit 10113 among the above-described constituents. Specifically, the imaging unit 10112 can be applied to a solid-state image sensor provided in the data source 12 illustrated in FIGS. 1, 5, and 8 to 13. The image processing unit 10113 can be applied to the data processing unit 14 illustrated in FIGS. 1, 5, and 8 to 13. By applying the technology according to the present disclosure to the capsule type endoscope used in the in-vivo information acquisition system, it is possible to achieve the miniaturization of the capsule type endoscope. Therefore, a load on a patient can be reduced. The capsule type endoscope has been exemplified as an application example to the in-vivo information acquisition system. However, the technology according to the present disclosure can also be applied to a wired endoscope, and thus can be used for an interface connecting an imaging unit provided in the wired endoscope and an external control device. By applying the technology according to the present disclosure to the wired endoscope, it is possible to achieve the miniaturization of the wired endoscope. Therefore, a load on a patient can be reduced.

The embodiments of the present technology are not limited to the above-described embodiments and can be changed in various forms within the scope of the present technology without departing from the gist of the present technology. The advantageous effects described in the present specification are merely exemplary and are not limitative and other advantages effects can be realized.

For example, the present technology can be configured as follows.

(1)

A transmission device including:

an oscillator configured to oscillate a first clock signal; and a control signal reception unit configured to receive a control signal transmitted from an external device and used for controlling the first clock signal.

(2)

The transmission device according to (1), including:

a storage unit configured to store a setting value of a frequency of the first clock signal oscillated by the oscillator.

(3)

The transmission device according to (1) or (2), including:

a data transmission unit configured to transmit data input from a data generation unit to the external device.

(4)

The transmission device according to (3), wherein the data transmission unit includes a divider that divides the first clock signal input from the oscillator and generates a second clock signal with a lower frequency than the first clock signal, a parallel-serial conversion unit that converts data input in a parallel form from the data generation unit in synchronization with the second clock signal into data with a serial form synchronized with the first clock signal, and a transmission driving unit that transmits the data with the serial form synchronized with the first clock signal to the external device.

(5)

The transmission device according to (4), wherein the data transmission unit transmits a signal for embedding the first clock signal in the data to the external device.

(6)

The transmission device according to any one of (3) to (5), wherein the number of data transmission units disposed is a plural.

(7)

The transmission device according to any one of (1) to (6), including a clock signal transmission unit connected to the oscillator and configured to transmit the first clock signal to the external device.

(8)

A reception device including:

a signal generation unit configured to generate a control signal for controlling a first clock signal transmitted from an external device based on a comparison result obtained by comparing a reference clock signal with one of the first clock signal and a second clock signal which is based on the first clock signal; and a signal transmission unit configured to transmit the control signal generated by the signal generation unit to the external device.

(9)

The reception device according to (8), including:

a data reception unit configured to receive data transmitted from the external device in synchronization with the first clock signal.

(10)

The reception device according to (9), wherein the data reception unit includes a divider that divides a frequency of the first clock signal input from the external device and generates the second clock signal, and a serial-parallel conversion unit that converts data input in a serial form from the external device in synchronization with the first clock signal into a data with a parallel form synchronized with the second clock signal.

(11)

The reception device according to (9) or (10), wherein the data reception unit includes a storage unit that temporarily stores the data transmitted from the external device in synchronization with the first clock signal.

(12)

The reception device according to (9) or (10), wherein the data reception unit includes a reproduction unit that reproduces the first clock signal embedded in the data and transmitted from the external device from the data.

(13)

The reception device according to (9) or (10), wherein the number of data reception units disposed is plural.

(14)

The reception device according to any one of (9) to (13), including a clock signal reception unit configured to receive the first clock signal transmitted from the external device.

(15)

A transceiver system including:

a transmission device configured to transmit predetermined signals; and a reception device configured to receive the predetermined signals transmitted from the transmission device, wherein the transmission device includes an oscillator that oscillates a first clock signal which is one of the predetermined signals, and a reception unit that receives a control signal transmitted from the reception device and used for controlling the first clock signal, and the reception device includes a signal generation unit that generates the control signal based on a comparison result obtained by comparing a reference clock signal with one of the first clock signal transmitted from the transmission device and a second clock signal which is based on the first clock signal, and a signal transmission unit that transmits the control signal generated by the signal generation unit to the transmission device.

(16)

The transceiver system according to (15), wherein bi-directional communication is able to be performed between the transmission device and the reception device.

REFERENCE SIGNS LIST 1, 2, 3, 4, 5, 6, 7, 8 Transceiver system
10A. 20A. 30A, 40A, 50A, 60A, 70A, 80A Transmission device
10B, 20B, 30B, 40B, 50B, 60B, 70B, 80B Reception device
11, 21, 31, 41, 51, 61, 71, 81 Transmission unit
12 Data source
13, 23, 33, 43, 53, 63, 73, 83 Reception unit
14 Data processing unit
111 Control unit
112 Oscillator
113 Register
114, 814 Register signal reception unit
115, 215 Data transmission unit
115a, 133c, 531, 711 Divider
115b Parallel-serial conversion unit
115c, 116a, 132a, 133a, 215c Driver
116 Clock signal transmission unit
117, 133e, 217, 233e Link unit
131 Control unit
132 Clock signal reception unit
133, 233 Data reception unit
133b Data synchronization unit
133d Serial-parallel conversion unit
134, 634 Signal generation unit
135, 853 Register signal transmission unit
216 Clock signal transmission unit
233b, 311, 312, 331, 332, 411, 412, 431, 432 Reproduction unit

The invention claimed is:

1. A transmission device comprising:
an oscillator configured to oscillate a first clock signal;
a control signal receiver configured to receive a control signal transmitted from an external device and used for controlling the first clock signal;
a data transmitter configured to transmit data input from a data generator to the external device, the data transmitter including a divider that divides the first clock signal input from the oscillator and generates a second clock signal with a lower frequency than the first clock signal, the data transmitter further including a parallel-serial converter configured to convert data input in a parallel form from the data generator in synchronization with the second clock signal into data with a serial form synchronized with the first clock signal, and transmission driving circuitry configured to transmit the data with the serial form synchronized with the first clock signal to the external device.

2. The transmission device according to claim 1, further comprising:
a memory configured to store a setting value of a frequency of the first clock signal oscillated by the oscillator.

3. The transmission device according to claim 1, wherein the data transmitter transmits a signal for embedding the first clock signal in the data to the external device.

4. The transmission device according to claim 1, wherein the transmission device includes a plurality of data transmitters, and the data transmitter is one of the plurality of data transmitters.

5. The transmission device according to claim 1, further comprising:
   a clock signal transmitter connected to the oscillator and configured to transmit the first clock signal to the external device.

6. A reception device comprising:
   a signal generator configured to generate a control signal for controlling a first clock signal transmitted from an external device based on a comparison result obtained by comparing a reference clock signal with one of the first clock signal and a second clock signal which is based on the first clock signal;
   a signal transmitter configured to transmit the control signal generated by the signal generator to the external device; and
   a data receiver configured to receive data transmitted from the external device in synchronization with the first clock signal, the data receiver including a divider that divides a frequency of the first clock signal input from the external device to generate the second clock signal, the data receiver further including a serial-parallel converter configured to convert data input in a serial form from the external device in synchronization with the first clock signal into data with a parallel form synchronized with the second clock signal.

7. The reception device according to claim 6, wherein the data receiver includes a memory that temporarily stores the data transmitted from the external device in synchronization with the first clock signal.

8. The reception device according to claim 6, wherein the data receiver includes reproduction circuitry configured to reproduce the first clock signal embedded in the data and transmitted from the external device from the data.

9. The reception device according to claim 6, wherein the reception device includes a plurality of data receivers, and the data receiver is one of the plurality of data receivers.

10. The reception device according to claim 6, further comprising:
    a clock signal receiver configured to receive the first clock signal transmitted from the external device.

11. A transceiver system comprising:
    a transmission device configured to transmit predetermined signals; and a
    reception device configured to receive the predetermined signals transmitted from the transmission device, wherein
    the transmission device includes an oscillator that oscillates a first clock signal which is one of the predetermined signals, and
    a receiver configured to receive a control signal transmitted from the reception device and used for controlling the first clock signal, and
    the reception device includes
       a signal generator configured to generate the control signal based on a comparison result obtained by comparing a reference clock signal with one of the first clock signal transmitted from the transmission device and a second clock signal which is based on the first clock signal,
       a signal transmitter configured to transmit the control signal generated by the signal generator to the transmission device, and
       a data receiver configured to receive data transmitted from the transmission device in synchronization with the first clock signal, the data receiver including a divider that divides a frequency of the first clock signal input from the transmission device to generate the second clock signal, the data receiver further including a serial-parallel converter configured to convert data input in a serial form from the transmission device in synchronization with the first clock signal into data with a parallel form synchronized with the second clock signal.

12. The transceiver system according to claim 11, wherein bi-directional communication is performed between the transmission device and the reception device.

* * * * *